(12) United States Patent
Doty

(10) Patent No.: US 10,881,523 B2
(45) Date of Patent: Jan. 5, 2021

(54) MOTION PRESERVING SPINAL TOTAL DISC REPLACEMENT APPARATUS, METHOD AND RELATED SYSTEMS

(71) Applicant: Keith L Doty, Gainesville, FL (US)

(72) Inventor: Keith L Doty, Gainesville, FL (US)

(*) Notice: Subject to any disclaimer, the term of this patent is extended or adjusted under 35 U.S.C. 154(b) by 0 days.

(21) Appl. No.: 16/027,498

(22) Filed: Jul. 5, 2018

(65) Prior Publication Data
US 2019/0008651 A1    Jan. 10, 2019

Related U.S. Application Data

(60) Provisional application No. 62/528,568, filed on Jul. 5, 2017.

(51) Int. Cl.
*A61B 34/10* (2016.01)
*A61F 2/44* (2006.01)
*A61F 2/30* (2006.01)

(52) U.S. Cl.
CPC ............ *A61F 2/4425* (2013.01); *A61F 2/441* (2013.01); *A61F 2002/305* (2013.01); *A61F 2002/30112* (2013.01); *A61F 2002/30235* (2013.01); *A61F 2002/30299* (2013.01); *A61F 2002/30474* (2013.01); *A61F 2002/30495* (2013.01); *A61F 2002/30528* (2013.01); *A61F 2002/30563* (2013.01); *A61F 2002/30649* (2013.01); *A61F 2002/30662* (2013.01); *A61F 2002/30841* (2013.01); *A61F 2002/30985* (2013.01); *A61F 2002/443* (2013.01); *A61F 2002/444* (2013.01)

(58) Field of Classification Search
CPC .................................................... A61F 2/4425
See application file for complete search history.

(56) References Cited

U.S. PATENT DOCUMENTS

| | | | | |
|---|---|---|---|---|
| 7,517,363 | B2* | 4/2009 | Rogers ................. | A61F 2/4425 623/17.11 |
| 8,231,677 | B2* | 7/2012 | Duggal ................. | A61F 2/4425 623/17.14 |
| 8,308,812 | B2* | 11/2012 | Kellar ................. | A61F 2/30767 623/18.11 |
| 9,308,101 | B2* | 4/2016 | Doty ....................... | A61F 2/442 |
| 2005/0043804 | A1* | 2/2005 | Gordon ................... | A61F 2/442 623/17.16 |
| 2006/0241767 | A1* | 10/2006 | Doty ...................... | A61F 2/4425 623/17.12 |
| 2008/0015693 | A1* | 1/2008 | Le Couedic ....... | A61B 17/7062 623/17.11 |
| 2008/0243253 | A1* | 10/2008 | Levieux ................ | A61F 2/4425 623/17.16 |
| 2010/0324688 | A1* | 12/2010 | Doty ..................... | A61F 2/4425 623/17.16 |
| 2014/0012382 | A1* | 1/2014 | Doty ....................... | A61F 2/442 623/17.16 |
| 2015/0173911 | A1* | 6/2015 | Doty ....................... | A61F 2/442 623/17.16 |

* cited by examiner

*Primary Examiner* — Zade Coley
(74) *Attorney, Agent, or Firm* — Gerard H. Bencen, Esq.

(57) ABSTRACT

The present invention provides a next generation, closed profile, total disc replacement device with mechanical features designed to sustain, restrain and guide the larger motions required to preserve normal mechanical motion, while at the same time, providing a flexion component to guide and restrain the finer motions reached at the extremes of the mechanical motion preservation components.

9 Claims, 15 Drawing Sheets

MOTION PRESERVING SPINAL TOTAL DISC REPLACEMENT APPARATUS, METHOD AND RELATED SYSTEMS

Priority of previously filed provisional application no. No. 62/528,568, filed on Jul. 5, 2017, and which was at the time of filing of this application, is hereby claimed.

FIELD OF THE INVENTION

Motion preserving total spinal disc replacement devices, methods and systems.

BACKGROUND OF THE INVENTION

When a biological disc between adjacent spinal vertebrae fails, pain, reduced flexibility, reduced motion, and other adverse effects result. To date, there have been efforts to address such biological failures, particularly in the cervical and lumbar regions of the spine, by a variety of techniques ranging from non-invasive, palliative approaches, to removal of the disc and fusion of the adjacent vertebral bodies to each other. More recently, a series of non-fusion Total Disc Replacement (TDR) technologies have been developed wherein one form or another of a motion preserving TDR device is inserted between the adjacent vertebrae, with the almost diametrically opposing objectives of (a) providing spinal stability while (b) preserving motion at the affected spinal disc and vertebral segments.

Thorough reviews of this art area are provided, for example, in "Motion Preservation Surgery of the Spine: Advanced Techniques and Controversies", by James J. Yue, Rudolph Bertagnoli, Paul C. McAfee, Howard S. An, (2008), and in "Spinal Arthroplasty: The Preservation of Motion", by Alexander R. Vaccaro, Stephen Papdopoulos, Vincent C. Traynelis, Regis W. Haid, and Rick C. Sasso., (2007). A further recent survey of the art area of spinal cervical disc replacement is provided by Richard D. Guyer, M D, Chairman of the Texas Back Institute Research Foundation, and is available at: https://www.spineuniverse.com/treatments/surgery/cervical/cervical-artificial-disc-replacement-technology-overview), relating to the seven currently FDA approved devices in the United States, namely: the Prestige© Cervical Disc; the Bryan© Cervical Disc; the ProDisc-C; the PCM dic; the Secure©-C; the Mobi-C©; and the Prestige© LP.

Notwithstanding progress to date, multiple reports in the peer-reviewed literature indicate that short and longer-term outcomes from spinal fusions or TDR replacements are less than ideal. It is therefore apparent that an ongoing and long-felt need exists for additional options for surgeons and patients to provide stability between adjacent vertebrae, while at the same time, preserving as normal as possible motion at the disc replacement and adjacent segment(s).

SUMMARY OF THE INVENTION

The present invention provides a next generation, closed-profile, total disc replacement device with mechanical features designed to sustain, restrain, constrain, stabilize, and guide the larger motions required to preserve normal mechanical motion of a spinal joint, while at the same time, providing a flexure component to guide and restrain/constrain the finer motions reached at the extremes set by the mechanical motion preservation components. In a preferred embodiment according to the invention, the device, referred to herein as the NFS-1 Device, comprises a closed-profile, meaning the device is a unitary component which does not come apart with normal physiologic forces, once assembled and implanted into a patient in need of such treatment.

Two principal embodiments of the NFS-1 device according to this invention include: a first principal embodiment, in which the device is assembled by a non-snap-fit method for associating the device components to each other, referred to herein as the NFS-1NSF embodiment, a particular example of which is referenced as D1 in FIGS. 1A, 1B, 2, and 3A; and a second principal embodiment in which the device is assembled by snap-fit method for associating the device components to each other, referred to herein as the NFS-1 SF embodiment, a particular example of which is referenced as D2 in FIG. 3B. Within these two principal embodiments, those skilled in the art will appreciate commonality of components as well as in the configuration and functioning of the fully assembled device. At the same time, those skilled in the art will appreciate that many of the components may be varied and that equivalents of such components may be utilized to advantage, without departing from the core features of the present invention as defined in the claims.

A third example embodiment D3, illustrated in FIGS. 21 through 26, depicts a variation in the top and bottom endplates and the introduction of a cushion rings (1700 and 2000), elements that can be employed in all embodiments of this invention. Those skilled in the art will appreciate the commonality of components in D3 to those in D1 and D2 as well as the configuration and functioning of the assembled devices.

The cushion rings introduced in D3 interact with the Ring-Joint-Stop (RJS) to protect the RJS and retainer plate from impingement damage that would be caused by rotations exceeding their Range-of-Motion (ROM). As soon as the RJS contacts a cushion ring, additional motion is resisted by the flexure properties of the cushion ring. The flexure properties and the thickness of a cushion ring govern the device response to rotations, once the RJS makes contact with the ring.

BRIEF DESCRIPTION OF THE DRAWINGS

FIG. 29B shows a tilted, frontal-section view, revealing curvate right-lateral bearing element (3351) and curvate left-lateral bearing (3251) as well as a curvate posterior bearing element (3250, with curvate anterior bearing element 3350, not shown, opposite 3250); FIG. 29C, shows a half-quadrant (of 3200), illustrating the difference in the maximum height of the two bearings: maximum height (3252) for curvate posterior bearings (3250), and maximum height (3253) for curvate left-lateral bearings (3251), while, similarly, a maximum height for curvate anterior bearing (3350 not shown, is 3352, also not shown) and maximum height for curvate right-lateral bearing (3351, designated by 3353), is revealed in FIG. 29B.

Figure 1:
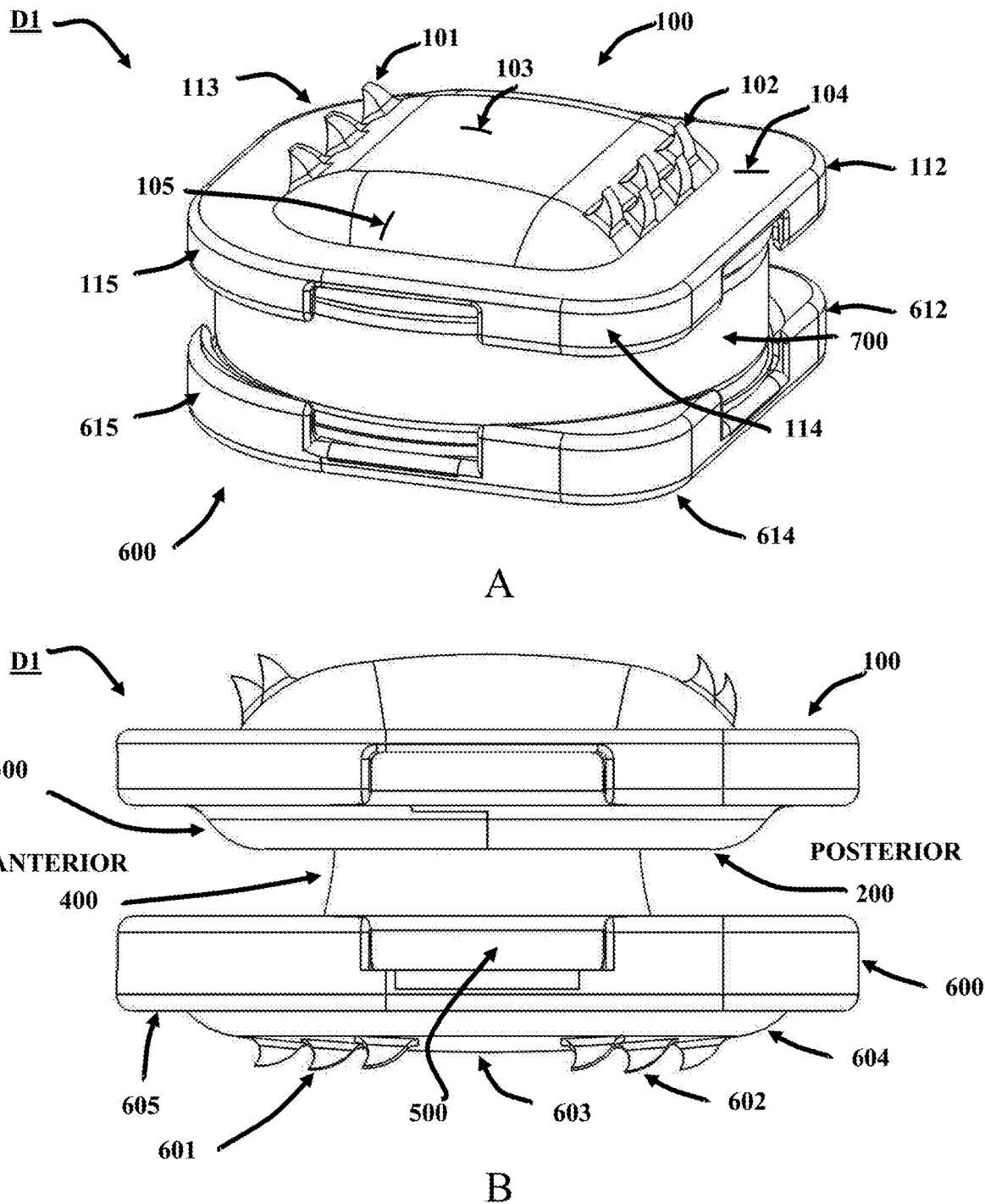
FIG. 1 presents a dimetric view in FIG. 1A, and an elevational view in FIG. 1B, of a non-snap-fit (NSF) embodiment D1 of the NFS-1 device according to this invention, i.e. NFS-1NSF.

DETAILED AND ENABLING DESCRIPTION OF PREFERRED EMBODIMENTS ACCORDING TO THE INVENTION AND EQUIVALENTS THEREOF

An objective of the present invention is to provide a Total-Disc-Replacement (TDR) device, system, and method, referred to herein as the NFS-1 device or the NFS-1 disc or the NFS-1 TDR device, for functional replacement of one or more damaged intervertebral spinal disc(s), wherein the disc replacement respects the natural anatomy and movement of the adjacent vertebrae between which it is implanted, to provide stability while also maintaining motion within physiologically acceptable limits.

As described in further detail herein below, the NFS-1 device according to this invention comprises, in all embodiments thereof, a top endplate 100, comprising a top surface for engaging with the underside of a superior vertebral body, and a bottom endplate 600 comprising a bottom surface for engaging with the top surface of an inferior vertebral body. A nucleus 400 comprising a curvate top "dome" portion, a core portion, connecting said curvate top dome portion to a substantially planar bottom "foot" portion, and said foot portion. While the nucleus 400 including its dome, core and foot are all described in further detail in the description which follows, for clarity, it is here noted that the several "portions" described here are either unitary or connected to each other so as to form a unitary nucleus 400. The dome of nucleus 400 is retained in contact with a mating curvate top endplate undersurface, to provide a closed-profile joint. The foot of nucleus 400 is likewise retained within a cavity in bottom endplate 600 in connection with which it is translationally engaged, so as to form a closed profile joint, as further described in detail herein below. Accordingly, it should be understood that the present invention provides a device which is a closed-profile device, by virtue of including two internal closed profile joints—one between the nucleus dome and the top endplate and one between the nucleus foot and the bottom endplate. Two principal embodiments of the NFS-1 device according to this invention include: a first principal embodiment, in which the device is assembled by a non-snap-fit method for associating the device components to each other, referred to herein as the (D1) or NFS-1NSF embodiment; and a second principal embodiment, in which the device is assembled by a snap-fit method for associating the device components to each other, referred to herein as the (D2) or NFS-1 SF embodiment. Within these two principal embodiments, those skilled in the art will appreciate commonality of components as well as in the configuration and functioning of the fully assembled device. At the same time, those skilled in the art will appreciate that many of the components may be varied and that equivalents of such components may be utilized to advantage, without departing from the core features of the present invention as defined in the claims. In either principal embodiment, the NFS-1 device according to this invention is a device comprising a top endplate, a bottom endplate, and an intermediate nucleus operationally connecting the top endplate and bottom endplate to each other, as further described herein.

The NFS-1NSF device, D1 in FIG. 1, according to this invention, comprises a top endplate 100, the upper surface of which interfaces with the bone of the lower surface of the superior vertebra of a Functional Spinal Unit (FSU) into which the invention is implanted. The top surfaces 103, 104, 105 of the device D1 and the two rows of teeth 101 and 102 present on the top surface of top endplate 100 are preferably treated to encourage bone attachment. This may include, for example, inclusion thereon of a rough titanium matrix of fractional millimeter pits, cavities, crevices, and similar surface features to establish long-term stability. The teeth 101, 102 provide immediate stability at the time of implantation to prevent any tendency of the NFS-1NSF embodiment of device D1 to back out of its site of implantation, pending bony ingrowth within the treated surfaces wherein permanent retention results.

Surrounding surface 104 provides a surface for purchase of cortical bone present in the periphery of the superior vertebral body, to prevent subsidence, while sheath 700 prevents biofouling of internal surfaces and mechanics of NFS-1 device D1. Sheath 700 is preferably comprised of a thin, extremely elastic, biocompatible material. Those skilled in the art will appreciate that a wide variety of materials now known, or which may hereinafter come into general use and acceptability for this purpose, may be used. In a preferred embodiment, a polycarbonate urethane (PCU), such as, but not limited to, Bionate® 80A, or a segmented polyurethane (SPU), such as but not limited to BioSpan®, is used to advantage for this purpose. Sheath 700 is preferably molded, extruded or otherwise manufactured to form a closed cylindrical shape. It is optionally provided with no folds or with different folding structures, including but not limited to accordion-shaped folds or other geometries known in the art or which are suggested by this disclosure to those skilled in the art.

Figure 18:
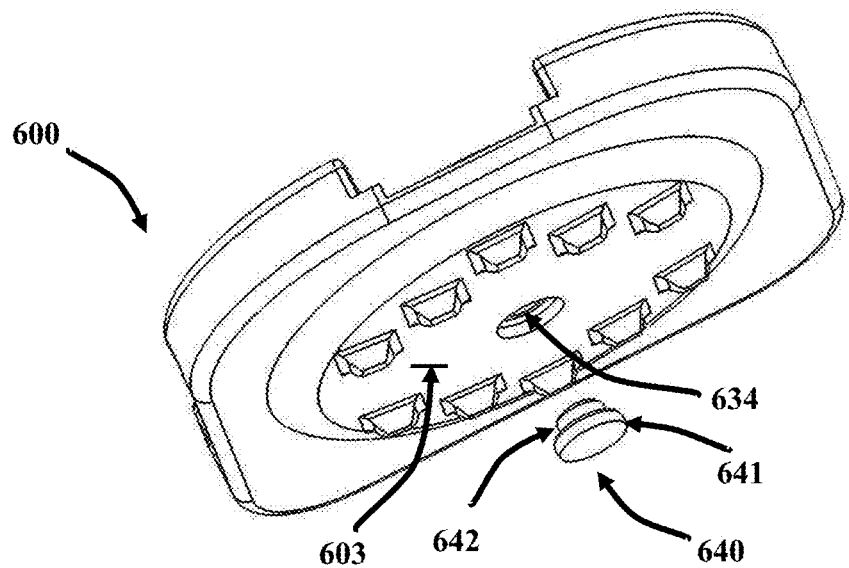
FIG. 18 shows a bottom endplate 600 with fluid access port 634 and port plug 640 which press-fits/laser-welds into 634. The lower edge of plug head 641 and plug stem 642 are chamfered for easier alignment. In a preferred embodiment, the plug head diameter exceeds the stem diameter, so as to present an insertion stop in port 634. A similar port and plug may be included in the top endplate 100, rather than the top endplate 600.
Figure 19:
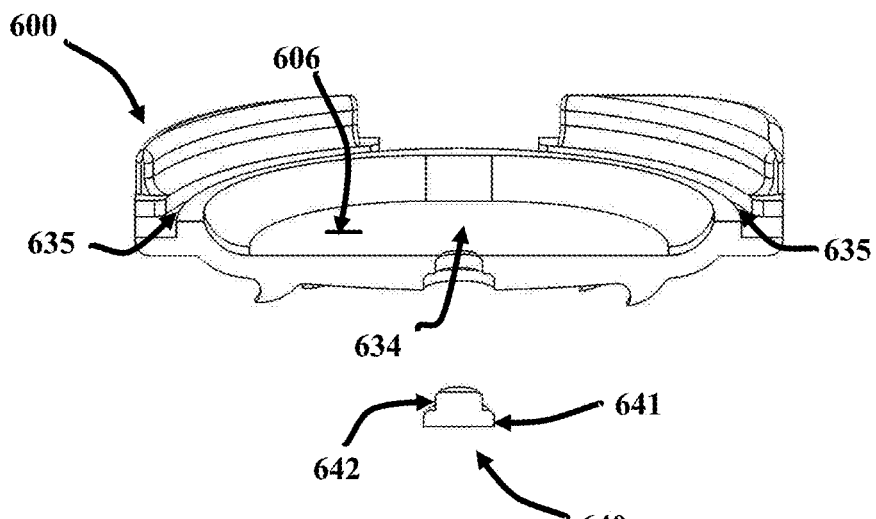
FIG. 19 presents a cross-section of the bottom endplate 600 with the plug 640 removed. The through port 634, with chamfers and insertion stop for the head 641, can clearly be seen.
Figure 20:
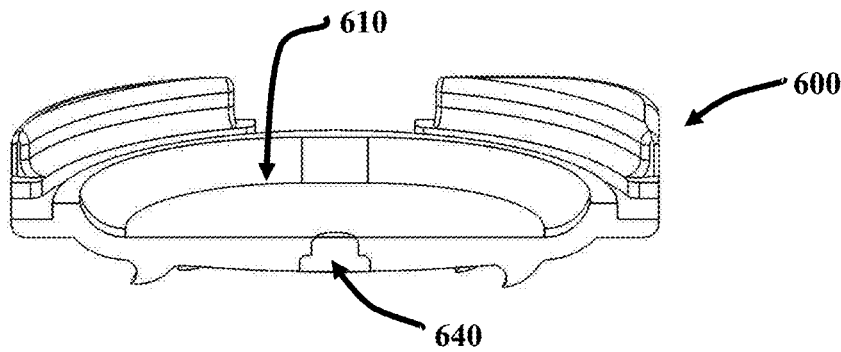
FIG. 20 depicts a cross section of bottom endplate 600 with plug 640 fully inserted. The top surface of head 641 conforms to the spherical surface 603, and the end surface of the stem 642 conforms to the surface 606.
Figure 21:
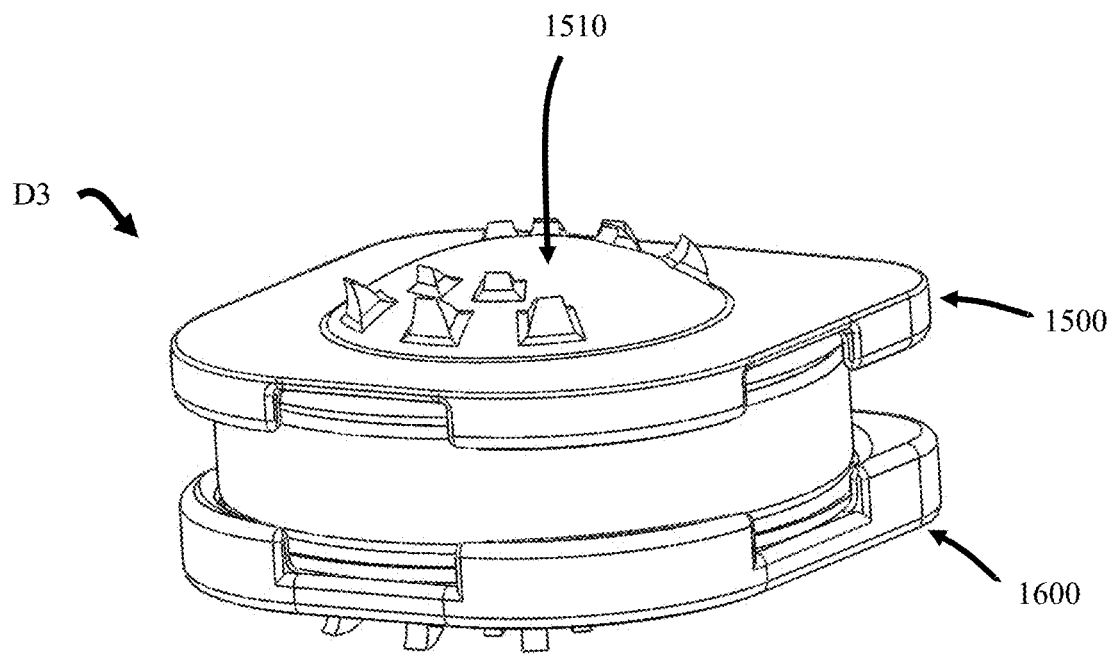
FIG. 21 illustrates a third embodiment D3 of the invention with a spherical outer surface 1510 and retention teeth structure on the top (1500) endplate. and bottom (1600) endplates.
Figure 24:
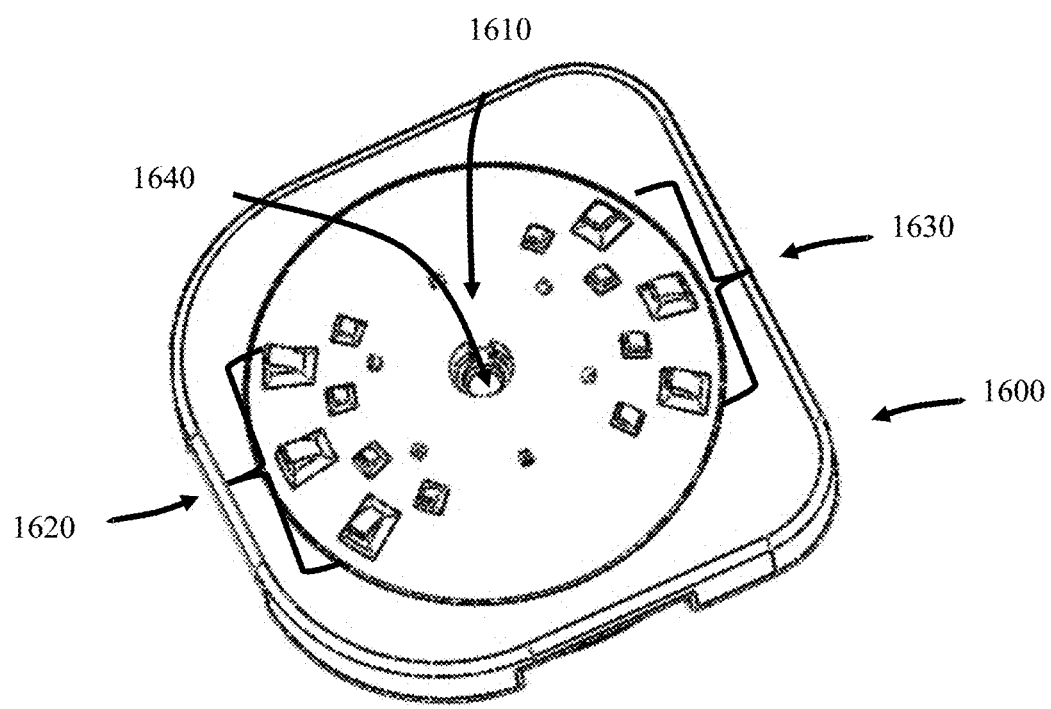
FIG. 24 details the bottom spherical surface of the bottom endplate. The dome 1610 has a larger radius of curvature than 1510 of the top endplate and has a different arrangement and sizes of the fixation teeth (1620 and 1630). The portal 1640 now has a keyed slot to prevent rotation of the plug (1900) shown in FIG. 27.
Figure 25:
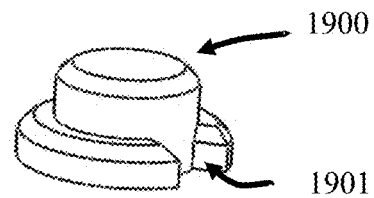
FIG. 25 images a keyed portal plug that press fits or welds, or both, into the bottom endplate portal 1610. This differs in the portal plug 640 in FIG. 19, which has no key slot to prevent rotation of the plug within the portal.
Figure 26:
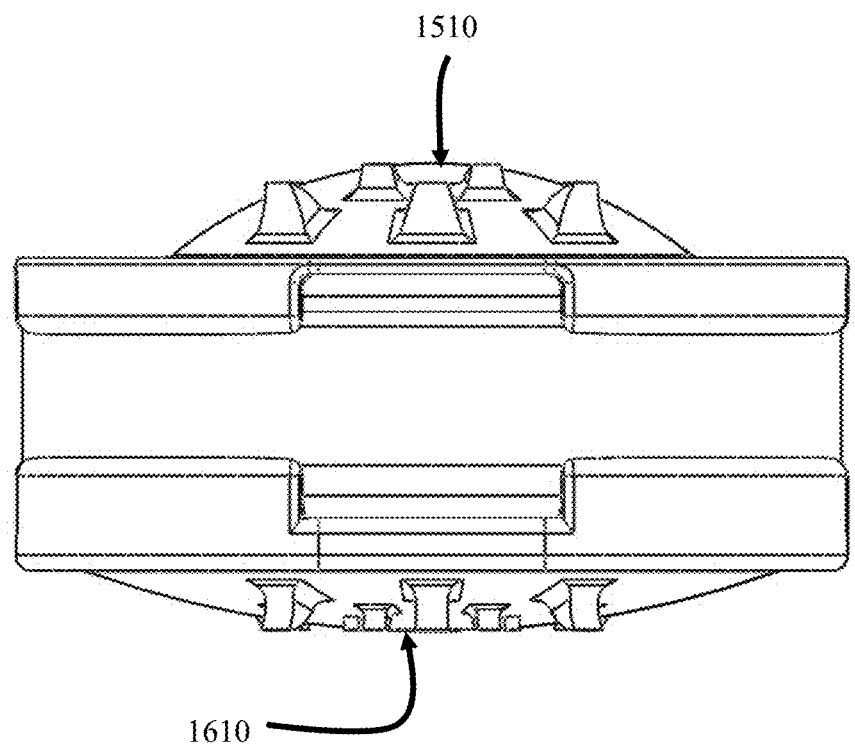
FIG. 26 presents a front view of D3 and clearly shows the different dome curvatures of the two endplate outer surfaces and the arrangement of fixation teeth.

Sterile fluid is optionally included within the chamber delineated between sheath 700 and top endplate 100 and bottom endplate 600 of the device. Such fluid is preferably incorporated during manufacture, for which a port 634 (refer to FIG. 18, 19, and 20) or 1640 (FIG. 24) is optionally provided in bottom endplates 600 and 1600 (FIG. 24). Those skilled in the art reading the present disclosure will appreciate that a similar port and plug may be included in the top endplate 100, rather than or in addition to said port and plug described for said bottom endplate 600. Port plug 640 comprises a head 641 and a stem 642, whose lower edges are chamfered and whose end surfaces conform to the spherical surface 603 and flat surface 606 of the bottom endplate 600, respectively. In a preferred embodiment, the head 641 diameter exceeds that of the stem 642 diameter to provide an insertion stop for a press-fit/laser-weld joining of the plug into the port. Port 634 conforms to the geometry of the plug 640, including negative chamfers in the chamber of the port. This ensures a tight seal after the press-fit of the plug into the port.

The keyed port plug 1900 has the features of plug 604, but with the added feature of a slot (1901)) to mate with a fixed key which is part of the portal cavity 1640. The internal key of port 1640 limits the amount of rotational motion of the plug over time, giving added durability of the seal provided by the plug.

A coordinate system, or frame, defined in Figure3A, is incorporated to precisely define features of the invention. The origin of the frame is located at the center of curvature of the spherical dome portion 401 of the nucleus 400. In the neutral position, 901 defines the x-axis and 902, 903 define the y-axis and z-axis, respectively, of the frame. When the nucleus foot 403 is centered in the bottom endplate cavity 611 (FIG. 2), the origin is located as shown. The frame origin and axes move as does the turning center as the nucleus foot 403 slides about in the cavity 611. This feature offers some benefits as discuss later herein.

In FIG. 1A top endplate 100 includes posteriorly projecting surfaces 112 and 114 and anteriorly projecting surfaces 113 and 115, preferably including rounded corners, thereby defining support surface 104 which mates with cortical bone on the inferior surface of a superior vertebra in an FSU. These elements also provide some protection to upper portions of the sheath 700 and assist sheath retaining ring 801 in restraining the sheath to the top endplate 100. Similarly, posterior projections 612 and 614 and anterior projections 613 (not visible in this figure) and 615 support underneath planar surface 605 which mates with cortical bone constituting a ring of such bone at the superior surface of an inferior vertebra in any given FSU. These elements also provide some protection and restraining of the sheath 700 to the bottom endplate 600, in conjunction with retaining ring 802.

FIG. 1B illustrates a left lateral elevational view of the NFS-1 device with the sheath 700 and sheath retaining rings 801 and 802 removed for ease of viewing of internal components. The following features may be seen: top endplate 100, posterior 200 and anterior 300 ring-joint-stop components, and bottom endplate 600. When brought together, posterior 200 and anterior 300 ring-joint-stop components form a combined or assembled ring-joint-stop, or RJS. The RJS limits, by design, the Range-of-Motion (ROM) for left-right lateral bending and flexion-extension to within nominal disc ROM specifications, as further described herein below.

Also evident in FIG. 1B of the NFS-1 one can find on the bottom endplate 600, anterior fixation teeth 601, posterior fixation teeth 602, graded fillet 604 leading from spherical surface 603 to planar surface 605. Planar surface 605 mates with cortical bone surrounding peripheral aspects of the superior surface of the lower vertebra of an FSU within which the NFS-1 device is implanted. Preferably, all lower surfaces, 603, 604, 605 of bottom endplate 600 include or are treated to include features which encourage bone ingrowth as described herein above with respect to the top endplate 100 surfaces. The lower surfaces 603, 604, 605 of bottom endplate 600 preferably present a substantially flat and low curvature surfaces to lie on cortical bone of the inferior vertebra of the FSU to prevent subsidence.

From FIGS. 1, 2, 5, and 7, the nucleus dome (spherical section) 401 and the conforming spherical section concavity 106 of top endplate 100 comprise a 3-Rotational-Degrees-of-Freedom (3RDOF) spherical joint (ball-and-socket joint). Rotations about the x-axis 901 generates flexion-extension, rotations about the y-axis 902 generates axial rotation, while rotations about the z-axis 903 realizes left or right lateral bending.

As seen in FIGS. 2, 3, 7, and 11, nucleus 400 comprises three principal regions: a nucleus dome (spherical section) 401, a cylindrically symmetric core 402 about the y-axis with concave lateral surfaces, and a disc-shaped foot 403. Preferably nucleus 400 is comprised of a flexible thermoplastic, including but not limited to, for example, polycarbonate urethane.

The nucleus 400 (FIG. 11) provides multiple functionalities with its three principal features, dome 401, core 402 and foot 403. As mentioned above, the nucleus dome 401 mates with concavity 106 (see FIG. 5) present on the underside of the top endplate 100 to comprise a ball-and-socket joint with 3RDOFs. The lower planer surface 404 of nucleus foot 403 mates with bottom planar surface 606 of cavity 611 of the bottom endplate 600 to establish a planar joint with 3DOF, 2-Translational-Degrees of Freedom (2TDOF), about the x-axis 901and z-axis 903 and 1RDOF, axial rotation about the y-axis 902. The concave lateral surfaces of the core 402 allow nucleus 400 to expand outward during compression (increasing load), or inward during expansion (decreasing load) as load forces on the FSU top endplate vary during operation. Compression-Expansion (CE) provides an additional 1TDOF in the axial direction 902. In total, there are 7DOF, 4 rotational and 3 translational. Axial rotation of the nucleus, in a frictionless environment, has no effect on the axial rotation of top endplate 100 since the nucleus would just spin within the ball-and-socket joint. In reality, through friction effects, nucleus axial rotation can contribute some axial rotation to the top endplate, providing a modicum of inconsequential redundancy.

The axial rotation of the planar joint realized by the allowed relative motion between the foot surface 404 and bottom endplate surface 606, is unrestricted, regardless of the position of the nucleus within cavity 611. However, boundaries dictated by opening 501 in retainer 500 and cavity 611, form an enclosing cavity within which the nucleus foot 403, and, hence, the entire integrated nucleus 400 translates and axially rotates. The 2TDOF provided by the closed-profile planar joint thus created is restricted by the shape of the cavity and, hence, that shape determines the allowable translational motion of the nucleus within that cavity. Effectively, elements 500 and 600 provide a 3TDOF joint stop: one each in the x (901) and z (903) directions and one in the y (902) direction. The latter eliminates separation of the planar interfaces of the planar joint by no more than a fraction of a millimeter. By cylindrical symmetry of foot 403, the axial rotation of the nucleus-top-endplate combination has no effect on the translational joint stop limits enforced by the configuration of the retainer 500 and bottom endplate cavity 611. The spherical mating of the dome 401 of nucleus 400 and the concavity 106 provided on the underside of the top endplate 100 does not allow translational motion. The flexibility of the nucleus, however, does permit y-axis compression-extension. During compression of the nucleus 400, all three elements of the nucleus, dome 401, core 402, and foot 403 have space into which they can expand. For example, the volume of top endplate concavity 106 exceeds that of the dome 401, hence, allowing expansion for the dome. The relative rigidity of the top endplate, forces the expanded dome to retain the shape of a spherical section. Any x-z axis translations of the top endplate 100 and spherically mated nucleus 400 must occur in concert, according to that allowed by the planar joint as describe above.

Figure 2:
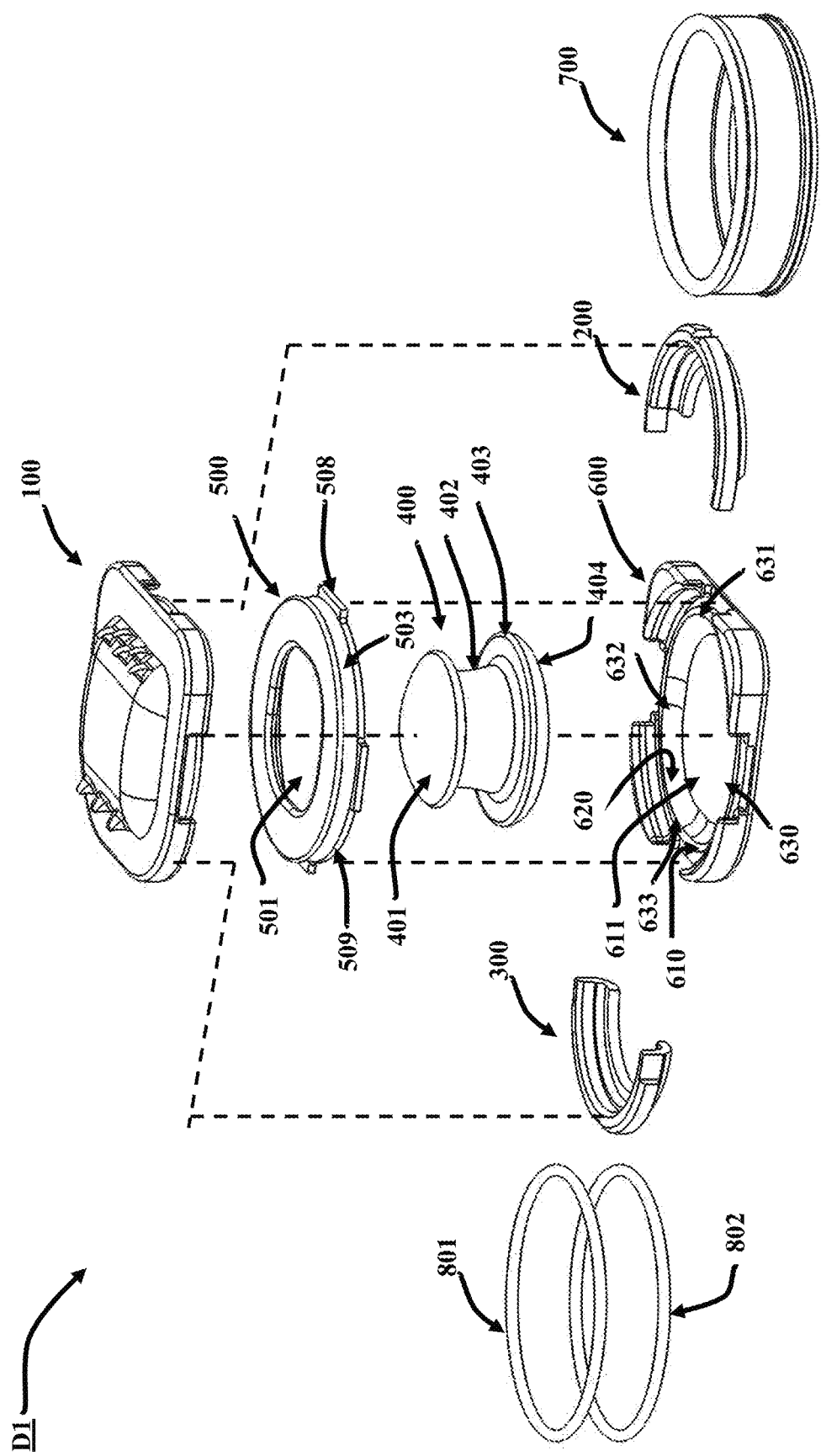
FIG. 2 shows an exploded image D1 of the NFS-1NSF device according to this invention. The teeth of the top and bottom end plates point anteriorly.

An exploded view of a non-snap-fit (D1) embodiment, NFS-1NSF, of the invention depicted in FIG. 2, illustrates the principal components of the invention: top endplate 100, nucleus foot retention ring 500 nucleus 400, bottom endplate 600, anterior RJS 300, posterior RJS 200, sheath 700, and sheath 700 retention rings 801 and 802. The fine dashed lines suggest assembly relationships between the components. Note here that the expanded elaboration of the bottom endplate 600, in particular the sheath and sheath retaining ring access "windows" 630, 631, 632, 633, retainer 500 insertion stop 610, a bottom endplate cavity designation 611, and concave spherical surface 620 forming a sloping wall of the cavity 611.

Figure 10:
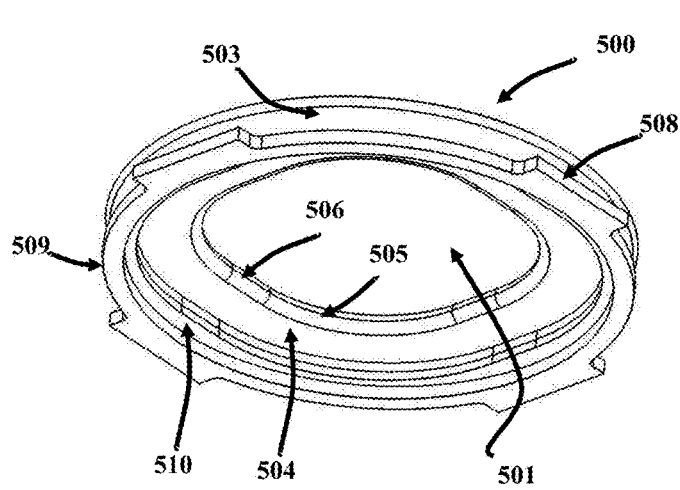
FIG. 10 depicts a retainer component 500 for retention of the nucleus component 400 of the invention for retention thereof within a bottom endplate cavity 611 of the NFS-1 device according to the invention.
Figure 11:
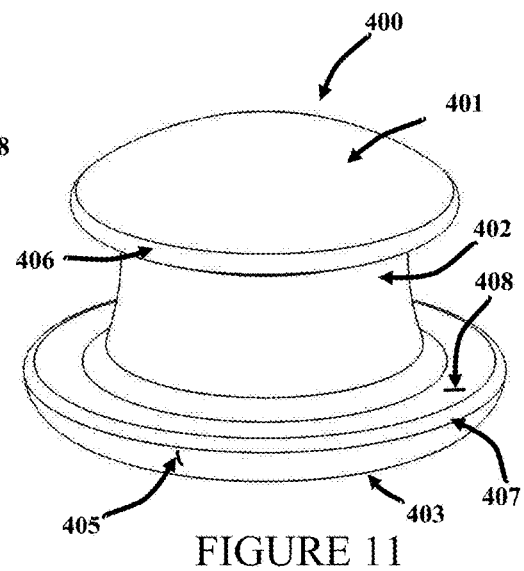
FIG. 11 shows a dimetric view of an embodiment of the nucleus component 400 of the NFS-1 device according to the invention.

In FIG. 3A, gap 904 equals d, the maximum translation of the planar joint in either the x or z direction: $-d \leq x \leq d$, $-d \leq z \leq d$. Cavity 611 has a unique shape to accommodate simultaneous x-z translation at the extremal points −d and d. In FIG. 10 boundary opening 501 comprises a rounded-corner-square with four straight edges 506 and four circular arcs 505 (refer to FIG. 10). The length of straight edge 506 equals 2·d. Boundary element 505 of 501 comprises four circular arcs whose radius of curvature equals the radius of curvature of the top edge, or lip 407 of foot 403 (FIG. 11). Four of these curvate boundaries seamlessly connect the four straight edges 506. At any of the extremal x-z positions of the nucleus foot 403, a nucleus curvate line 405 intersects in a curvate line 607 on curvate surfaces 620 or 621, shown in FIG. 4. The wall structure of cavity 611 (FIG. 2) of the bottom endplate employs a curvate structure 621 and 620 with the following property. The intersection of surfaces 620 and 621 (up to fillet 622) with any plane parallel to the zx-plane generates a closed curve equal to a rounded-corner square. The dimensions of the intersection boundary changes with the height of the intersecting plane above the zx-plane, reaching a maximum, for purposes of this discussion, when the intersecting plane coincides with face 408 on top of the nucleus foot 403. These comments apply to any embodiment of NFS-1.

FIGS. 2, 3, 7, and 11 provide further views of nucleus 400, which provides shock absorption, stability, and maintenance of intervertebral spacing. At the same time, the nucleus resists, through flexion of the nucleus dome 401 by the RJS in contact with 401, any rotational motions of the top endplate exceeding permissible flexion-extension (FE) or lateral bending (LB) Range-of-Motion (ROM). The translation joint stops dictated by the retainer 500 and bottom endplate cavity 611 resist, through flexion of the nucleus foot, any translation of the combined nucleus and top endplate which are constrained to translate together, that exceeds the ROM of the planar joint, as well as any forces which might otherwise tend to extract the nucleus 400 from its closed-profile cavity. In the NFS-1NSF embodiment (FIG. 1, FIG. 3A), orifice 501 of foot retainer 500 is large enough to permit passage there through of the nucleus dome 401, but not of the nucleus foot 403. The size differential between the maximum diameter of the foot 403 and the diameter of orifice 501 determines whether a non-snap-fit (NSF) or a snap fit (SF) assembly of the nucleus foot with the bottom endplate 600 is possible. In the latter case, retainer 500 integrates as a single unit with bottom end plate 600, and is preferably manufactured by molding, machining or using additive manufacturing techniques known in the art.

FIG. 3A presents a cross section of the NFS-1NSF device shown in FIG. 1. Evident from this view are at least the following features of a non-snap-fit device: separate posterior 200 and anterior 300 ring-joint-stop elements to retain nucleus dome 401 within spherical concavity 106 defined in the lower surface of top endplate 100; retainer 500 that is welded, press-fit, or both, with the bottom endplate 600 to retain nucleus foot 403 within cavity 611 defined within the upper aspect of the bottom endplate 600.

In its assembled state, the NFS-1NSF embodiment of the device allows 6 independent motion degrees-of-freedom between top endplate 100 and bottom endplate 600 without separation of either the spherical joint (ball-and-socket) or the planar joint within the device either prior to or when the device is implanted. Both joints are referred to herein as closed-profile joints and the invention as a whole comprises a 7DOF closed profile mechanical joint with flexion modalities, as further described herein. In such a device, an external force, not normally encountered physiologically, is required to separate the elements. This means the joint maintains functional and positional integrity throughout normal operation, including in zero gravity. The mechanics of the joint allow large mechanical motions of rotation, compression, and translation, while flexibility of the nucleus allows small flexure motions for all degrees of freedom when the joint is at one or more joint stops. In a preferred embodiment of the invention, all rotations, except axial rotation, and all translations, include joint stops to constrain motion within normal physiological limits. A central, preferably, polycarbonate urethane nucleus 400 comprises a spherical dome 401, a central core 402, and a disc-shaped foot 403. Exemplary and non-limiting examples of preferred materials for manufacture of the nucleus 400 include thermoplastics with appropriate stress-strain curves suitable for disc flexibility and stability. In one preferred embodiment of this aspect of the invention, the nucleus 400 is composed of DSM PCU 75D. This material is commercially available from DSM Biomedical Inc. under the trade name Bionate®.

Sheath 700 comprises a thin film molded, cylindrical sheath of highly elastic PCU, for example DSM's commercially available BioSpan®, protects the internal mechanism from biofouling until the body encapsulates the device with scar tissue. Upper and lower sheath retaining rings 801 and 802 preferably comprise elastomeric material exhibiting a transition temperature that is set at substantially below survival body temperature such that, at the transition temperature, the retaining rings are extremely flexible and slip tightly over the sheath's 700 upper and lower extremities, to retain the sheath termini within channels provided for this purpose in both the top and bottom endplates 100 and 600, respectively. At room temperature, which is above the transition temperature, the rings snap to their smaller memory size and tightly clamp the sheath against the raceways holding the sheath and rings. Accordingly, assembly of the sheath retaining rings 801 and 802 and sheath 700 is carried out at or below room temperature. The cylindrical sheath 700 is preferably stretched and tucked into each raceway provided about the periphery of the top and bottom endplates, 100 and 600, respectively. The retaining rings are initially positioned loosely around the middle of the sheath 700 and then forced into each raceway to provide a tight fit. At or above room temperature, the memory wire pops into its smaller memory state and clamps the sheath tightly against the raceway walls. In a preferred embodiment, without being limiting on use of other appropriate materials, each sheath retaining ring 801 and 802 is comprised of nitinol, which exhibits these desired thermal expansion and contraction properties.

Figure 3:
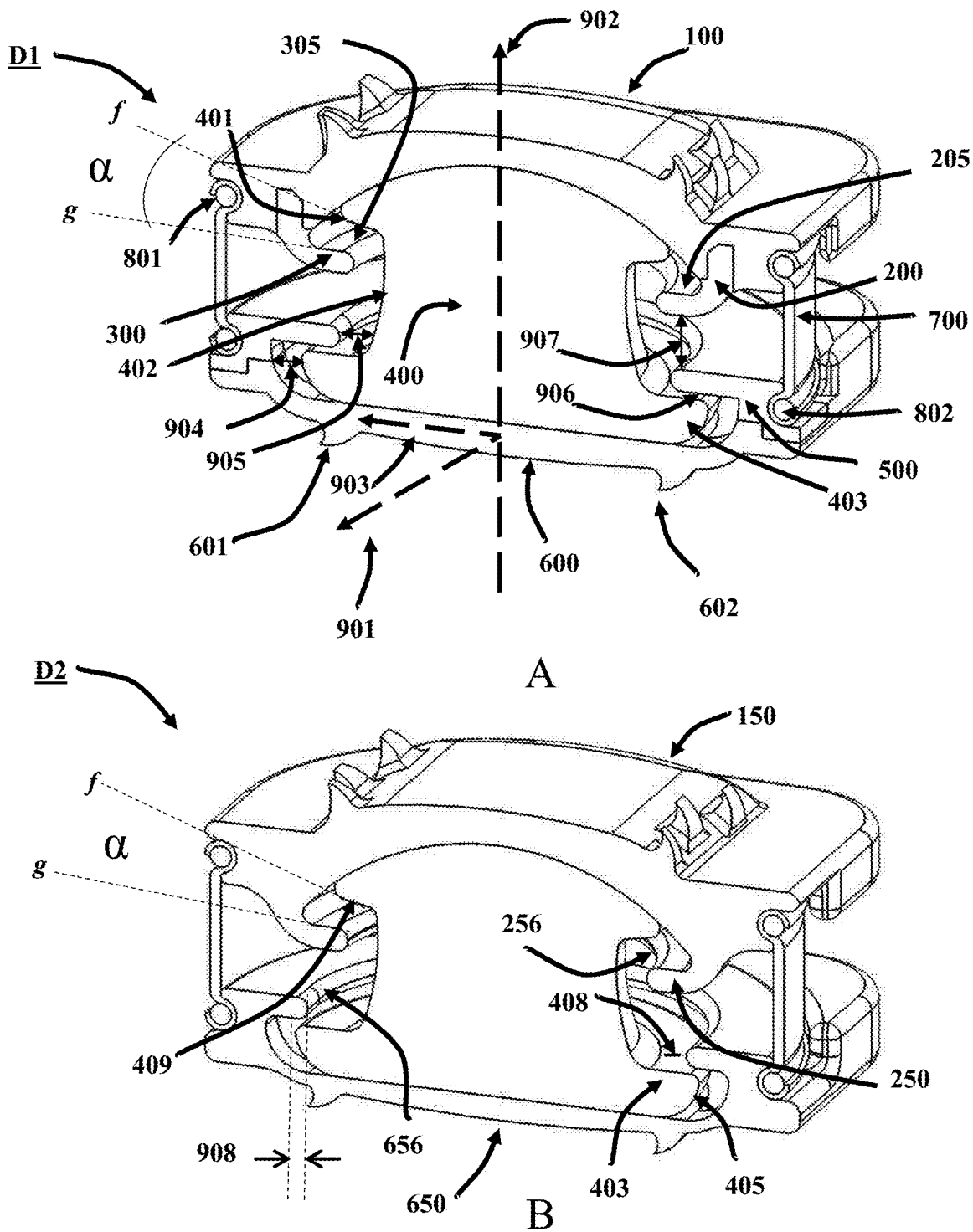
FIG. 3, comprised of FIGS. 3A and B, illustrate, respectively, a cross sectional view of the NFS-1NSF device D1 shown in FIG. 1 and a cross sectional view of an embodiment D2 of the invention assembled by means of a snap fit mechanism and methodology, named NFS-1SF.

Geometry 901, 902, and 903 denote the x-axis, y-axis, and z-axis, respectively, of top endplate 100 in the neutral position (as shown in FIG. 3) and of the nucleus in all cases, defining a coordinate frame whose origin is at the center of curvature of the spherical dome 401 of the nucleus 400 and the central spherical concavity in the inferior surface of the top endplate 100. As a result, as the nucleus moves, the center of curvature moves, thereby providing motion freedoms recognized as advantageous, such as, for example, by compensating for irregular motions and by lessening stress on the nucleus 400 and the overall device for such motions. Another advantage is greater tolerance in placement of the implant. For example, the center of curvature of the nucleus spherical dome can vary within a circle of diameter of 2 mm about the y-axis 902 as required for any particular embodiment, or TDR procedure.

Gap 904 between disc foot and a preferably curvate wall surface of an inner aspect of the bottom endplate 600 is, preferably about 1mm, depending on the particular embodiment, as required for a given TDR procedure. This gap is subject to adjustment, as needed, by altering the dimensions of disc-shaped foot 403, dimensions of the foot retaining space defined within the bottom endplate, 600, or both. Nucleus foot 403 retainer 500 in a non-snap-fit embodiment of the invention, i.e. NFS-1NSF, preferably comprises an orifice smaller than the diameter of foot 403. Assembly of retainer 500 with the bottom endplate 600 is achieved by press-fitting, by laser-welding, or both, of the retainer 500 to bottom endplate 600. Such assembly is conducted following slippage of the retainer 500 over the dome of the nucleus 400, the planar surface of which 404 rests on the bottom endplate 600 planar surface 606. A gap 906 between a lower inner surface of retainer 500 and the top of the nucleus foot lip in select embodiments varies from about 0.1 mm to about 0.25 mm, thereby reducing wear contact of the nucleus foot upper surface 406 (FIGS. 3 and 11) against the metal undersurface 504 of retainer 500, which, respectively, in preferred embodiments, are comprised of PCU and titanium, respectively.

In the neutral position, the overlap of the nucleus foot lip 407 (FIG. 11) with the retainer 500 is at least as large as the gap 904 between the tip of the foot and the closest cavity wall of the bottom endplate 600. Gap 905 between the edge of the retainer 500 and the wall of the nucleus core is preferably as large as gap 904, to thereby allow expansion of the nucleus core wall with compression. Gap 907 between both RJS elements and the top surface of the retainer 500 limits the amount of compression before impingement of the RJSs with the retainer occurs. The three gaps referred to here are all important design parameters. As further used herein, the term RJS means either the joint anterior, posterior or both, when from the context, it is clear that the RJS is being considered as a single entity or as the integrated RJS 250 of a snap-fit (NFS-1 SF) embodiment as part of top endplate 150 as shown in FIG. 3B.

As shown in FIG. 3A, angle α refers to the angle measured between the intersection of two lines f and g. Line f results from the intersection of the sagittal yz-plane, defined by y-axis 902 and z-axis 903, and underside surface of dome lip 406. Line g equals the intersection of the yz-plane with flat inner surface 305 of RJS 300. For the drawings of RJS in FIGS. 15 and 16, these latter surfaces are continuations of surface segments 1202 and 1402, respectively, since the yz-plane does not actually intersect those segments. In select embodiments according to this invention, α is, without being limiting, preferably about 10°. Angle α determines the degree of constraint on motion imposed by the RJS. For example, with the top endplate 100 horizontal to the zx-plane, the top endplate can realize any rotation angle less than or equal α about any axis in the zx-plane, regardless of the position of the nucleus on the planar surface 606 encompassed by bottom endplate 600. Thus, even an implant that results in a non-centered nucleus allows a rotations as just described. To illustrate, the RJS limits the ROM of a pure flexion or extension or lateral bend to the right or left by α. When the RJS meets this limit, as reflected in the angle α, it flexibly, but stiffly, limits rotations other than 1) axial rotations, i.e. rotations about y-axis 902 and 2) any rotation that disengages contact between the RJS and the dome lip 406. When the RJS is not engaged, the amount of lateral bending and flexion-extension permitted increases the further away the RJS moves from the limit angle α. Accordingly, those skilled in the art will understand from this disclosure that the RJS limit prevents impingement of the RJS with the retainer 500. Herein, below, alternate RJS designs are elaborated wherein the RJS permits 3) any rotation that did not cause the engagement of the RJS and the dome lip 406. As a simple example, if the top endplate rotates a in flexion, not only will a reversal of the direction of rotation disengage the RJS from the dome lip (number 2 above), but, as long as a left or right bending rotation has not reached a, too, then those rotations will not be resisted by the RJS (number 3 above). The latter rotations, however, will not disengage the RJS from its flexion limit.

A third example embodiment D3, illustrated in FIGS. 21 through 26, depicts a variation in the top and bottom endplates and the introduction of a cushion rings (1700 and 2000), elements that can be employed in all embodiments of this invention. Those skilled in the art will appreciate the commonality of components in D3 to those in D1 and D2 as well as the configuration and functioning of the assembled devices.

The cushion rings introduced in D3 interact with the Ring-Joint-Stop (RJS) to protect the RJS and retainer plate from impingement damage that would be caused by rotations exceeding their Range-of-Motion (ROM). As soon as the RJS contacts a cushion ring, additional motion is resisted by the flexure properties of the cushion ring. The flexure properties and the thickness of a cushion ring govern the device response to rotations, once the RJS makes contact with the ring.

Figure 27:
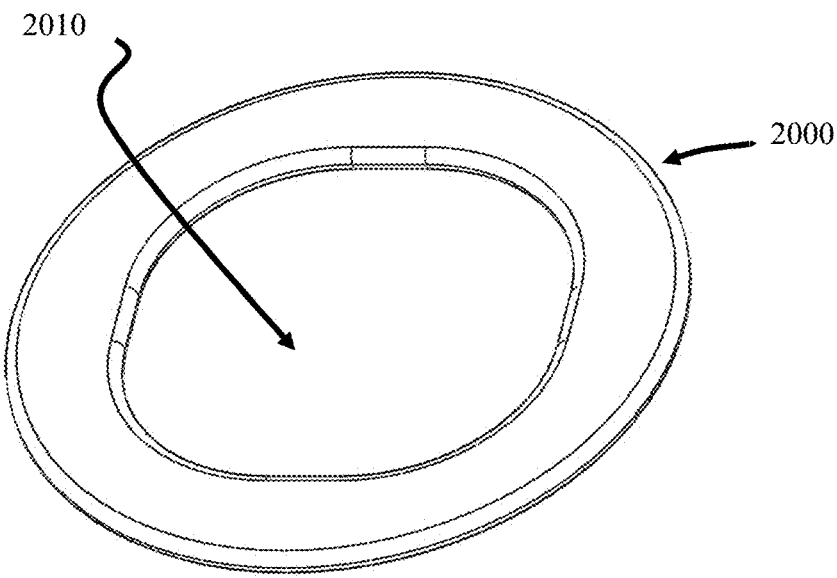
FIG. 27 features a cushion ring (2000) with a rounded-corners-square (rcsq) inner hole (2010) to allow true x-y planar motion of the nucleus within a rcsq cavity (610) in the bottom endplate 600 (See FIG. 20).

Cushion ring 2000 (FIGS. 27) lies on top of the retainer plate 500, or 653 which partially cover the rounded-corners-square cavity of their respective bottom endplate. Cushing ring 1700 lies on top of the integrated retainer plate 1650 of FIG. 22 which covers a circular cavity within the bottom endplate. These ring cushions can be thermoplastic PCU such as Bionate® with durometer ranging from 80A to 75D.

Figure 28:
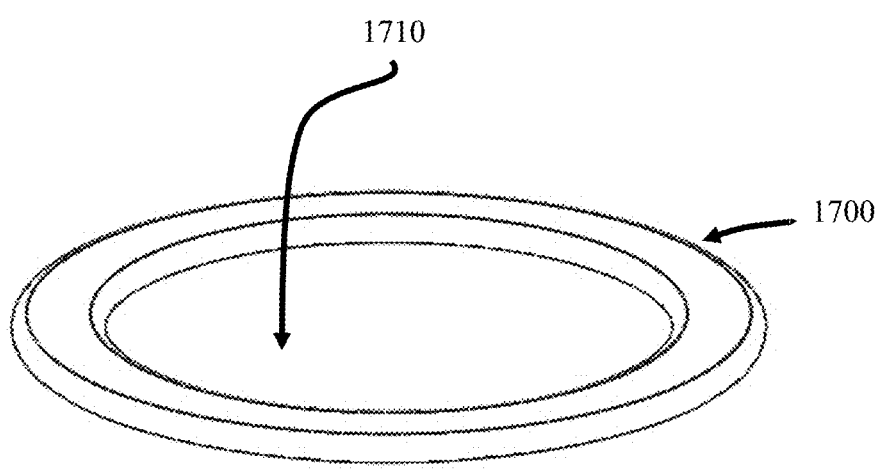
FIG. 28 illustrates a circular cushion ring (1700) with circular inner hole (1710) to allow polar coordinate planar motion of the nucleus in a circular cavity 1610 in bottom endplate 1600 (See FIG. 22).

One function of the cushion rings is to mitigate impingement damage and wear of the RJS and the retainer plate in all models by providing a soft joint stop. A second function is to provide a resistive force as the cushion is compressed. For example, suppose the angle α=10° then the cushion thickness can be made so that contact begins at 8°. Compression of the cushion between 8° and 10° will resist the rotation with greater and greater force, impeding overdriving the rotation beyond its specified Range-of-Motion (ROM). A third function of a cushion ring is to relieve the stress on the dome lip by carry the greater load burden generated by overdriving the rotation. Axial rotations have no device implemented constraints. Axial constraints, however, will be constrained by spinal structures. The cushion rings provide resistance to rotations (except axial ones), dependant on the thickness of the cushion ring, i.e. the angle at which the RJS contacts the cushion ring. Further, the cushion ring hole matches the allowed planar motion allowed by the bottom endplate cavity, namely, either circular: polar-planar (angle, radius); or rounded-corners-square: x-y planar (see FIGS. 27-28).

Figure 4:
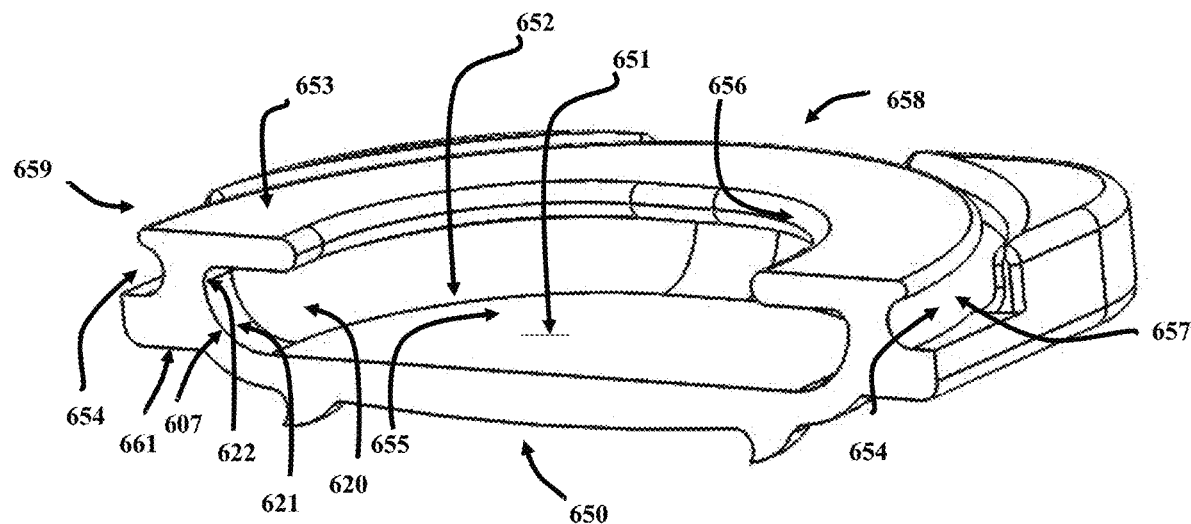
FIG. 4 provides a sectional image of a bottom endplate 650 of an NFS-1SF (D2) embodiment of the invention.

Referring now to FIG. 3B, a perspective cross sectional view of the NFS-1 SF (D2) device, assembled via a snap-fit mechanism and methodology, is described. In this embodiment of the invention, referred to as the NFS-1 SF device, the nucleus 400 snap-fits into either or both the top and bottom endplates. While the embodiment shown in FIG. 3B includes both an upper and lower snap fit mechanism by means of which the nucleus 400 attaches to the top endplate 100 and the bottom endplate 600, in other embodiments, only the top or the bottom of the nucleus snap-fits. In such cases, the non-snap-fit assembly proceeds as described above in connection with the embodiment shown in FIG. 3A. Such embodiments are included within the scope of this invention.

Where both top and bottom extremities of the nucleus 400 are assembled with top endplate 100 and the bottom endplate 600 by a snap fit mechanism, as shown in FIG. 3B, such embodiments eliminate the need for separate Ring-Joint-Stops (RJS) 200 and 300 as well as separate retainer 500. Rather, in the embodiment of FIG. 3B, top endplate 150 comprises an integrated and unitary Ring-Joint-Stop (RJS) 250, with edge boundary 256, which comprises a rounded corner square as described for 656. Bottom endplate 650 integrates retainer feature 656 to eliminate the need for a separate retainer 500. In such embodiments, nucleus dome 401 snap-fits into the conforming spherical section concavity 106 of top endplate 150. Nucleus foot 403 snap-fits into central cavity 655, as shown in FIG. 4, of bottom endplate 650. The material, e.g. plastic, polymer or other flexible, biocompatible material, selected for nucleus 400, dictates the distance 908 for the snap-fit between the tip of retaining lip 656 and the tip or lip 407 (FIG. 11) of nucleus foot 403, with nucleus 400 centered.

By contrast with non-snap-fit embodiments of the invention, (e.g. the NFS-1NSF embodiment shown in FIG. 1A), separate retaining elements, retainer 500 does not allow the nucleus to snap-fit through orifice 501. In such embodiments, distance 908 is too large for a snap-fit, making the joint separation force larger than in the snap-fit embodiments of the invention, NFS-1SF, such as that shown in FIG. 3B.

Referring now to FIG. 4, a perspective sectional view of a NF S-1SF embodiment of the invention is depicted comprising a retainer integral and unitary with the bottom endplate 650. In a preferred embodiment, bottom endplate 650 allows nucleus 400 to snap-fit into bottom endplate cavity 611 without requiring a separate retaining ring 500. Overhang 653 retains the nucleus 400 after snap-fit assembly. Bottom endplate 650 integrates the retaining ring 500 and bottom endplate 600 into a single unified structure suitable for snap fit assembly. An undercut for snap-fit (SF) embodiments is preferably sufficiently small to allow traditional machining options. In a preferred embodiment, the unitary bottom endplate 650 is molded, machined, or most preferably, manufactured by 3D printing/additive manufacturing methods known in the art.

Cavity 655 houses nucleus foot 403. Overhang 653 prevents nucleus foot 403 from unforced disassembly due to interference between the leading edge of the foot lip and the overhang lip 656. Orifice 652 is dimensioned to permit snap-fit insertion of nucleus 400. Planar section 651 constituting the floor of the bottom plate cavity, preferably comprises a rounded corner square, the linear sides of which equals twice the length of gap 904. Preferably, the rounded corners comprise radii of curvature similar or preferably identical to that of the retained nucleus foot 403 at the tip of its lip 407, thereby allowing the nucleus foot to translate in the plane from (0,0), the center of the coordinate system specified in relation to FIG. 3A, to any (x,0, z) position, wherein $-d \leq x \leq d$ and $-d \leq z \leq d$ where d=|gap 904|, the magnitude of the gap distance 904. At the extremals, where |z| or |x| equals d, the nucleus is constrained in its ability to translate in one or two of the four directions (two directions per x-axis and two per z-axis), which translations are possible from the center position. For example, at the four rounded corners |z|=|x|=d and the nucleus can only translate away from the corner. At all positions, the nucleus can rotate about the y-axis of its moving frame, i.e., axial rotation. While assembled by different mechanisms, these planar translational considerations apply equally to both the snap fit and non-snap-fit embodiments of the invention.

When nucleus 400 compresses under load, nucleus foot 403 can expand into the bottom endplate, limiting translations of the nucleus foot 403. Under extreme compression loads, greater than 500N, the space can fill almost entirely and, thus, flexibly, but stiffly resist any translation of the nucleus 400, and possibly axial rotation of the nucleus, due to greatly increased cavity-foot friction or cramming. In this situation, the planar joint can be blocked, and the nucleus will be unable to translate along either the x-axis or z-axis. The loss of those freedoms, however, can actually be beneficial by offering greater stability of the implant under heavy loads.

Circular raceway 654 allows sheath retaining ring 802 to clamp the lower edge of the sheath 700 to bottom endplate 650. Four openings 657, 658, 659 and 660 (not visible in this view) are spaced 90 degrees apart in the lateral walls of 650. These openings allow access to the retaining ring 802 that may be required, depending upon choice of assembling ring 802 to clamp the sheath 700 to the bottom endplate. Planar surface 661 of bottom endplate 650 provides the same features as surface 605 of bottom endplate 600 and serves the same purposes, namely, to provide a surface for the bottom endplate to rest on the ring of cortical bone of a superior surface of an inferior vertebra of an FSU.

Figure 5:
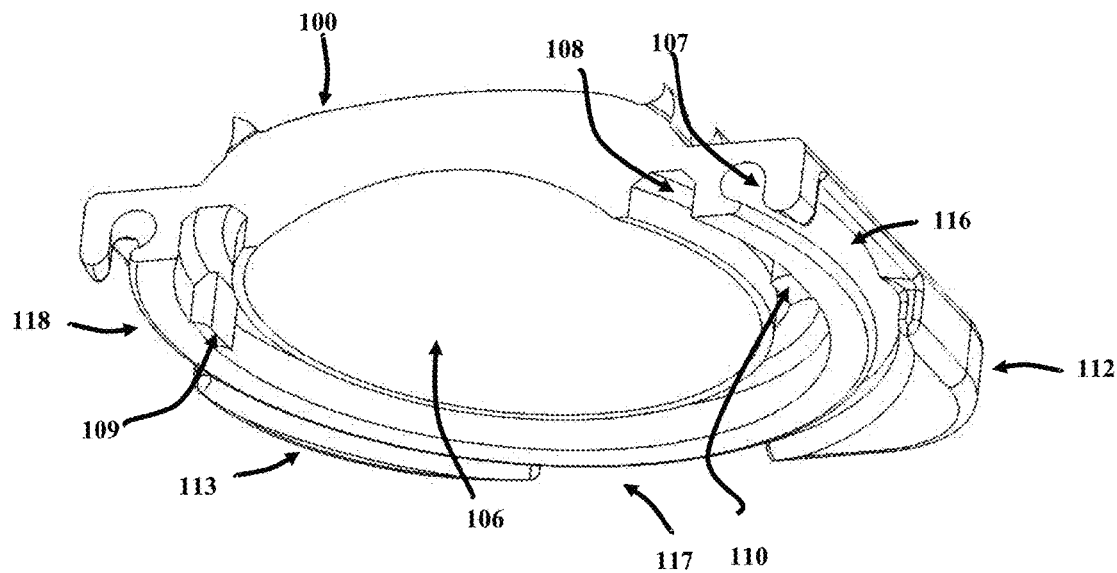
FIG. 5 depicts a sectional view of the top endplate component 100 from below of the NFS-1 device according to the invention.

Referring now to FIG. 5, there is provided a bottom perspective sectional view of top endplate 100, which reveals at least the following features: spherical section concavity 106 which is adapted to mate with the dome of nucleus 400 to comprise a spherical joint with three degrees of rotational freedom with no restriction on axial rotation (about the y-axis 901). This spherical joint also permits +α degrees rotation about any axis k in the z-x plane, axes 903 and 901, respectively. When axis k equals the z-axis 903, then the rotation can be identified with left-right lateral bending, whereas when k equals the x-axis 901, the rotation becomes identified as flexion-extension. At an angle +α about k in the z-x plane, the RJS of FIG. 6 engages the lip of the dome and a cushion ring 2000 or 1700 whereupon only axial rotations are permitted. To regain full three degrees of rotational freedom, the RJS must rotate away from the dome lip. For example, a flexion of α degrees engages the posterior portion of the RJS and the anterior portion of a cushion ring, provided the latter's thickness is set for α degrees. Preferably, the cushion ring thickness should be such that it is engaged several degrees before the dome lip to avoid excessive stress on the lip. To disengage the RJS from the dome lip in this example, the flexion angle must be reduced, at which point all three rotational degrees of freedom become available once again. The three independent angular motions available at the "back-off" point is a function the angular distance between the RJS and the dome lip.

Figure 6:
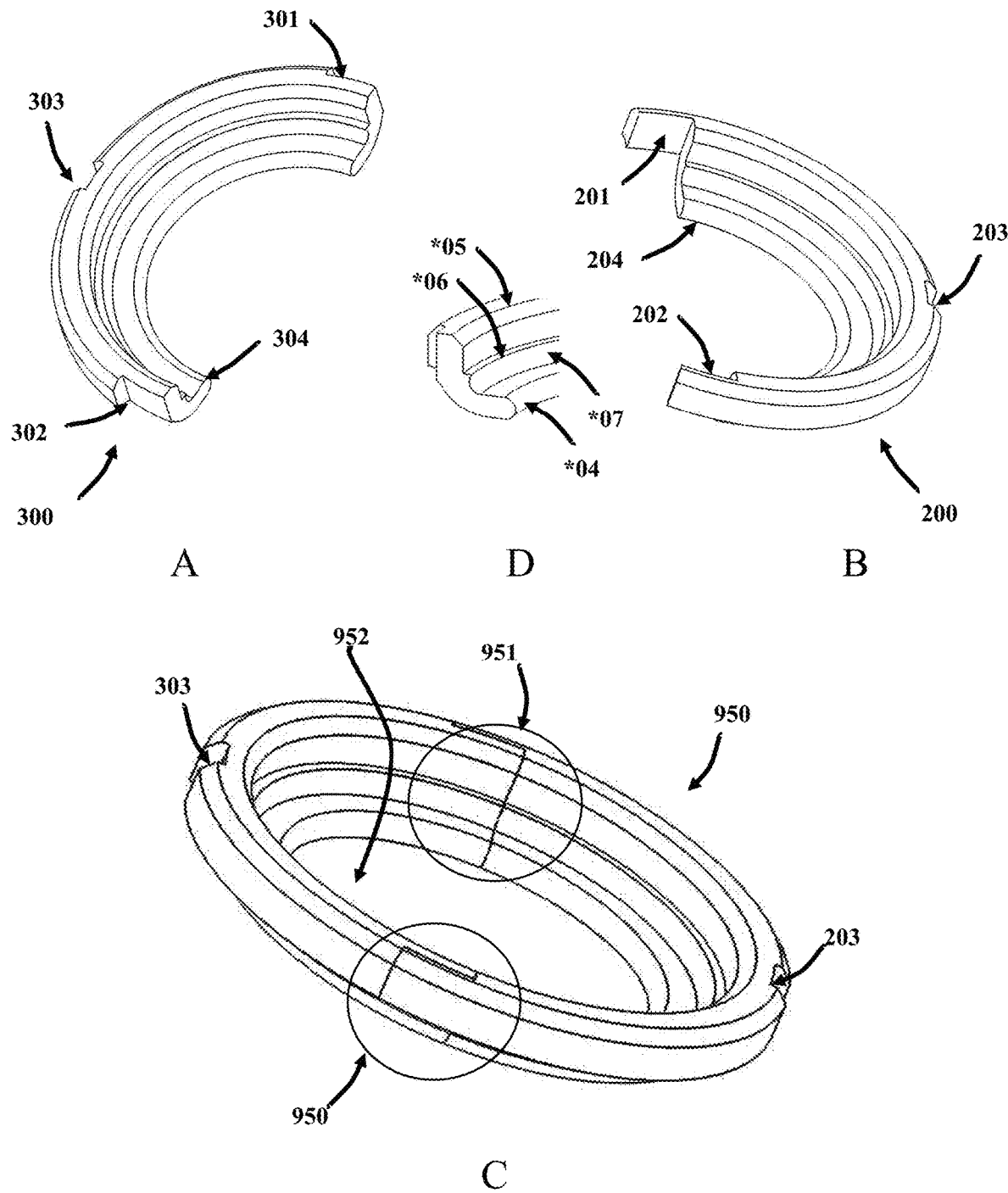
FIG. 6, comprised of FIGS. 6A, B, C, and D, illustrate, respectively, the anterior Ring-Joint-Stop (RJS) 300, posterior RJS 200, assembled RJS, and detailed surfaces of either component of the NFS-1NSF (D1) embodiment of the invention, respectively. To reduce redundancy, the "*" simultaneously represents either "2" for RJS 200 or "3" for RJS 300, e.g., "*05" represents both "205" and "305".
Figure 22:
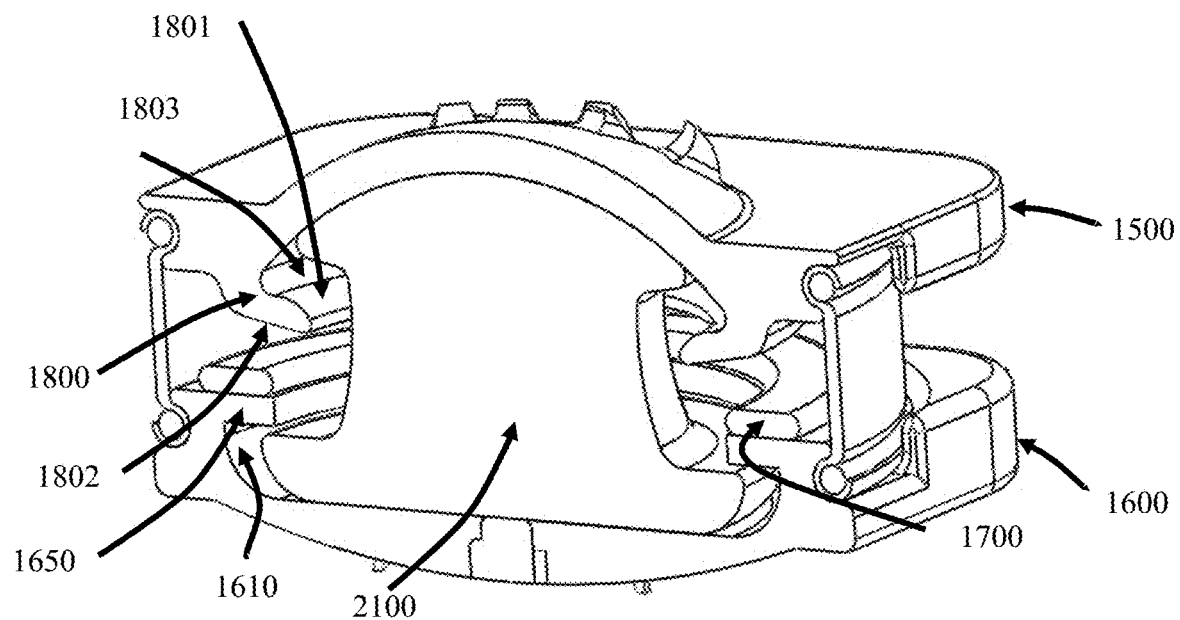
FIG. 22 provides a section view of the D3 clearly indicating similar structures to D1 and D2 with the addition of the cushion ring 1700 and a Ring-Joint-Stop (RJS) 1800 whose lower surface slopes at a fixed angle.
Figure 23:
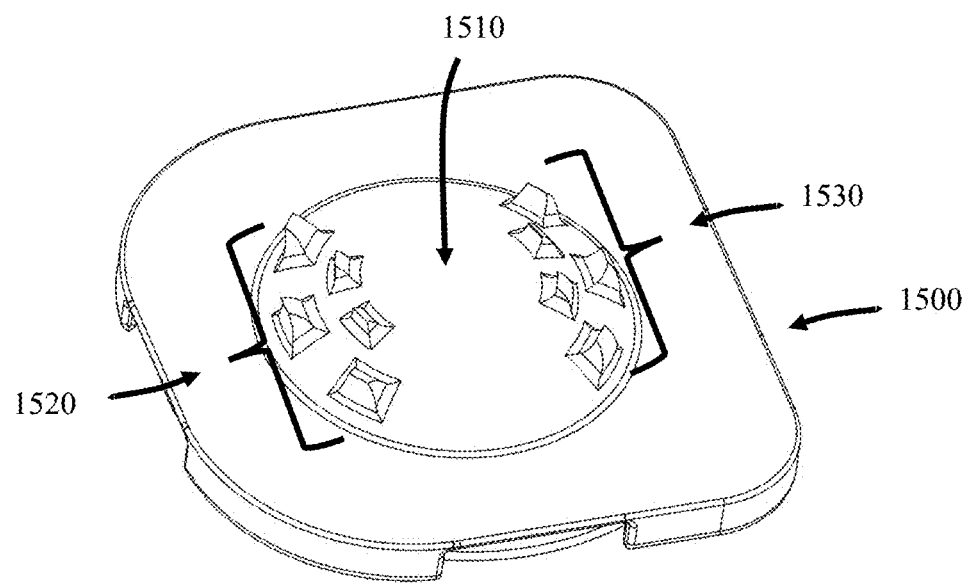
FIG. 23 shows the dome structure of the outer surface of the top endplate (1500) and the spherical arrangement of the fixation teeth anteriorly (1520) and posteriorly (1530).

The RJS (1800) in FIG. 22 operates as the one in FIG. 6, but has different curvature on its upper surface 1801 and lower surface 1802. The curvature of 1801 comprises two fillets, the lower fillet having a larger radius of curvature than the upper one in order to increase the line of contact with the dome lip at maximum rotation. The curvature 1802 is, in fact, a straight line created by the intersection of any plane section passing through the y-axis and RJS. This line is at α degrees so that entire line contacts the cushion ring 1700 for any rotation of α degrees about any axis k in the zx-plane.

For the two preferable RJSs depicted in FIGS. 14, 15, 16, and 17, the analysis in the previous paragraph does not apply. Those two preferable embodiments provide the superior property of independent ROM for Flexion-Extension (FE) and right-left Lateral Bending (LB). Even if one of the two angles is at α degrees, the other angle remains operable. In contrast, 1) in a compound rotation of FE and LB to achieve the same orientation of the top endplate that is produced by a rotation +α about kin the zx-plane, and 2) if that orientation requires either FE or LB to be greater than α degrees, then 3) the RJS would engage the dome lip 406 before achieving that equivalent orientation. Simply stated, in such a case, the top endplate orientation produced by rotation +a about a particular kin the zx-plane would not be realizable by the physiological based ROM of FE and LB of the preferred embodiments. In this sense, the preferred RJS embodiments in FIGS. 14, 15, 16, and 17 provide a more precise physiologic control of FE and LB. (See FIG. 5). An RJS press-fit, laser welded, or both, into raceway 108, enables permanent fixation to the top endplate 100 during the lifetime of the device. In a preferred embodiment, hard stops 109 and 110 are provided in the raceway to prevent internal axial rotation of the RJS that might otherwise act to work the lap joined anterior 300 and posterior 200 RJS halves (FIG. 6) loose. Hard stops 109 and 110 are integrated into the machining or additive manufacturing of the top endplate 100. An integrated RJS 250 in a snap-fit embodiment 150 of the top endplate is evident in FIG. 3B. Sheath retaining ring 801 fits into raceway 107 and clamps sheath 700 to the top endplate 100. Window openings 116, 117, 118, and 119 (the latter not visible in this representation), which are distributed about the periphery as shown, permit access to the sheath ring.

Figure 7:
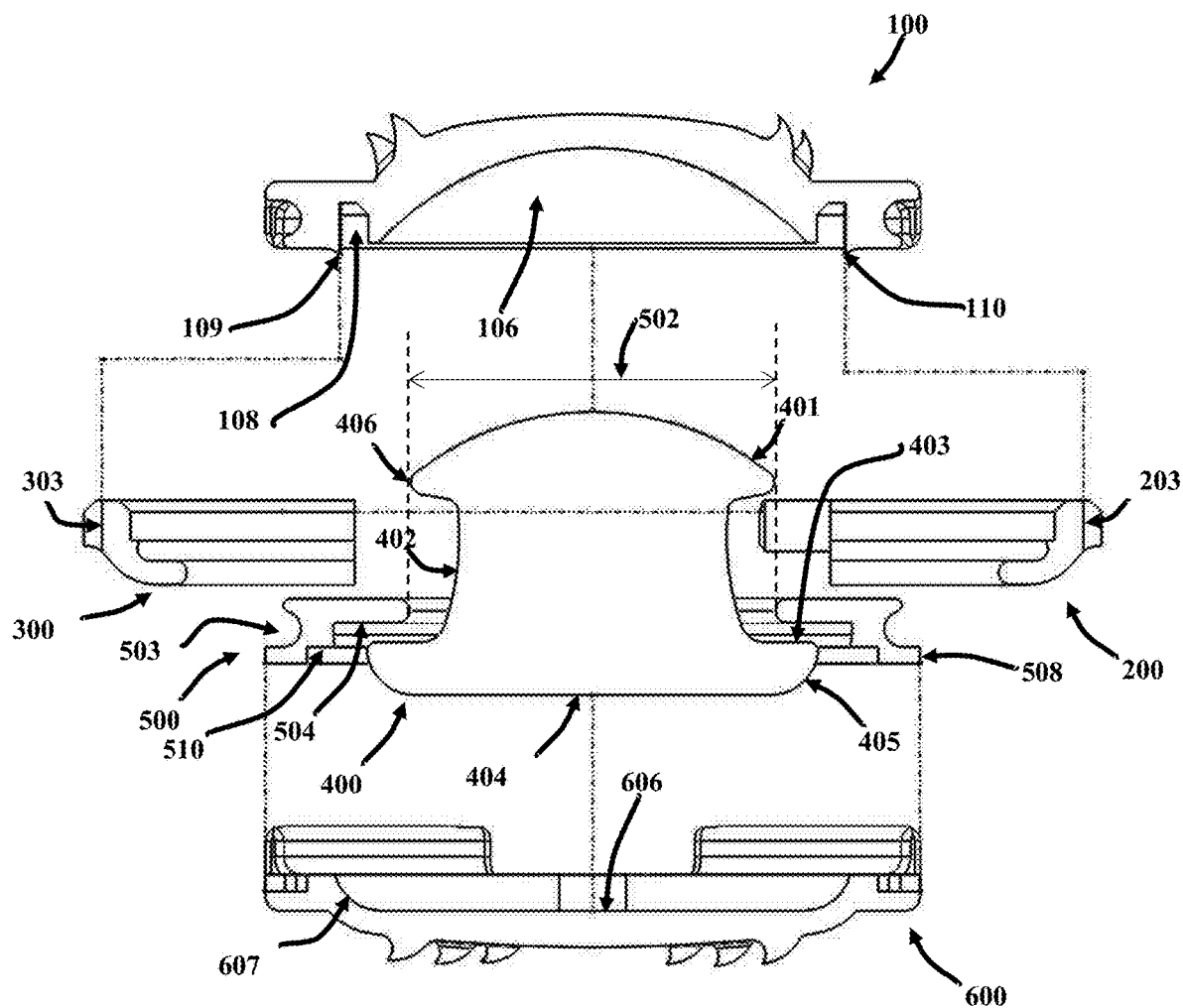
FIG. 7 projects a planar, elevated view of a non-snap fit (D1) embodiment of the invention, NFS-1NSF, without showing the sheath or sheath retaining rings, to enhance ease of representation of internal elements that would be obscured if the sheath were shown in place. The fine dashed lines show assembly connections and the two vertical coarser dashed lines lay out distance 502.

FIGS. 6A, B and C, illustrate anterior, posterior and assembled views of the RJS. Anterior RJS (ARJS) 300 and posterior RJS (PRJS) 200 mate together at two lap joints 950 and 951 to form a unified RJS (or simply, RJS) 950 to thereby create an enclosing aperture, or orifice 952 which is too narrow to allow the dome 401 of nucleus 400 to pass through, resulting in assembly consequences as shown in FIG. 7 and described in detail previously. This orifice is bounded by elements 204 and 304.

Lap joint 950 is formed by the overlay of elements 202 on 302 and lap joint 951 is formed by the overlay of elements 201 and 301. Slots 203 and 303 are preferably provided to allow registration of the ARJS and the PRJS with elements 109 and 110 on the top endplate 100 during assembly, as further described below in relation to FIGS. 6 and 7. Assembly is by press-fit, laser weld, or both into raceway 108 of the top endplate 100. Elements 109 and 110 further serve the function of eliminating axial rotation within raceway 108.

For the indicators *04 through *07 in FIG. 6D, the numbers 2 or 3 can be substituted for the "*", to define alternate embodiments 204-207 and 304-307. Element *05 comprises a chamfered insertion ring section with insertion stop *06. A ring insertion stop *08, not visible in this representation, similar to *06 is optionally provided to the outer lateral surfaces of the ARJS 300 and PRJS 200, for ease of assembly. Features 1205 in FIGS. 14 and 1404 in FIG. 17 incorporate such lateral surface insertion stops for those RJS embodiments.

Element *07 is a curvate surface that conforms to the curvature of the dome lip 406 as further described herein below in relation to FIG. 7. When the top endplate 100 rotates α degrees about any axis in the zx-plane, surfaces *07 and *04 contact nucleus dome lip 406. Upon contact, further rotation is resisted by the nucleus through flexure thereof. Dome lip 406 and nucleus core 402 compress, stretch or both at the curvate lines of contact.

Referring now to FIG. 7, there is provided a view of a non-snap fit embodiment of the invention, NFS-1NSF, without showing the sheath to enhance ease of representation of internal elements that would be obscured if the sheath were shown in place. Because of the closed-profile nature of the joint embodied by the invention, its assembly requires a specific sequence of mating of the component elements. Distance 502 of orifice 501 of retainer 500 preferably permits nucleus dome 401 to pass through 501 without interference. Accordingly, a first assembly step is to pass retainer 500 over the top of the nucleus dome 401. Not shown is that a cushion ring 2000 with the same size and shape hole as that of retainer can lie on top of the retainer as it is placed in position (Refer to 501 FIGS. 2 and 2010 FIG. 27). In this example, there is no adhesive or mechanical fitting of the cushion to the retainer. Foot 403 prevents the nucleus from passing fully through retainer 500. Next, the RJS is emplaced around the nucleus core. The joined elements ARJS and PRJS of the RJS create an opening 952 that prevents passage of both the nucleus dome 401 and the nucleus foot 403. The maximum diameter of core 402, however, is smaller than opening 952, thus, splitting the RJS into two component elements, ARJS and PRJS, permits these elements to be separately assembled around the nucleus core. The top endplate spherical section concavity 106 (FIG. 5) provides a conforming concentric surface with the nucleus dome spherical section 401 (FIG. 2). These conforming surfaces then are mated. RJS elements 300 and 200 are manipulated below the dome lip 406 for insertion into raceway 108 (FIG. 5), while, simultaneously, cavity 109 is mated with projection 303 and cavity 110 is mated with projection 203, bringing lap joints into mating position for laser spot welding on their external surfaces, to thereby combine to form the completed RJS.

The RJS elements 300 and 200 are fitted together and then press-fit, spot welded, or both, into top endplate 100, thus encapsulating the nucleus dome 401 in a closed-profile ball-and-socket arrangement.

Retainer 500 in FIG. 10 embodies a ring feature 509 with four elements 508 that press-fit/weld into raceway 635 of bottom endplate 600. Insertion stop 510 contacts matching ledge 610 to limit the insertion. Elements 508 fit into the window openings 630, 631, 632, 633 (FIG. 2) of the bottom endplate 600 and oppose axial shear on the retainer after fixing. The rounded corner square boundary shape of aperture 501 has a similar geometry to the base cavity. Four linear sections 506 are connected by four circular sections 505 that have the same radius of curvature. The aperture 501 is large enough to accommodate translation motions of nucleus 400 as well as compression expansion of the core 402. Flat surface 504 in preferred embodiments does not contact the nucleus foot surface 408 (FIG. 11) except under extreme compression of the nucleus 400 or during moments-of-force generated by the RJS against the dome lip at angle limits. The latter moments-of-force tend to extract the nucleus from cavity 611 (FIG. 2) or 655 (FIG. 4) and generates contact between surface 408 and 504 that prevents such extraction. After assembling retainer 500 with bottom endplate 600, a closed-profile planar joint is created.

In this embodiment of the invention, such means for assembly is dictated by 1) the aperture diameter of the assembled RJS, 2) the opening afforded by the complex boundary of aperture 501 and 3) the radii of the dome 401, core 402 and foot 403. Specifically, the dome 401 can pass through the aperture 501 but the foot 403 cannot. This first requires insertion of dome 401 of nucleus 400 through the retainer opening 501. Neither the dome 401 nor foot 403 can pass through the diameter of the assembled RJS. The RJS, after assembly, confines the top endplate 100 to the dome 401 of the nucleus to create 1) the desired closed profile ball-and-socket joint while simultaneously, 2) enabling ROM control for right-left lateral bending and flexion-extension, and 3) help protect the FSU from possible impingements or damage due to excessive motions produced with non-closed-profile joints.

The assembled RJS limits the maximum vertical separation of the top endplate spherical concavity 106 from the nucleus dome 401. In the neutral position, this separation is less than about 1.0 mm before *04 of the RJS interferes with the undersurface of the dome lip 406. This interference is sufficient to flexibly resist further vertical separation under normal physiological forces.

Retainer 500, which now rests on the top of foot 403, is press-fit into, and laser welded to, bottom endplate 600, thereby pulling nucleus 400 into the bottom endplate cavity 611 for retention therein. At final assembly, the top surface of foot 403 clears retainer undersurface 504 by more than about 1.0 mm. Surface 404 contacts surface 606 upon provision of a slight amount of pressure on top endplate 100, hence, forming a closed-profile planar joint under normal spinal loads.

Filleted surface 405 of the nucleus 400 reduces the area, and, hence, friction of the planar joint formed between surface 404 and surface 606 of the bottom endplate 600. Filleted surface 405 also permits a larger thickness at the thin part of the outer inferior surface of bottom endplate 600 as this curves the cavity away from that surface. This feature is readily apparent from the cutaway sections shown in FIGS. 3 and 4.

Raceway 503 of retainer 500 allows sheath retaining ring 802 to firmly press sheath 700 against the raceway wall. Sheath 700 preferably comprises a thin film of highly flexible polycarbonate urethane, segmented polyurethane, or similar plastic and may optionally include accordion or like folds to eliminate stress on the film during and post implantation. As discussed above, a sterile fluid may likewise be included within the chamber defined by the sheath 700 in combination with top endplate 100 and bottom endplate 600. Sterile fluid is injected into the device after assembly and sterilization, through the portal 634 in the undersurface of the bottom endplate 600 and permanently sealed within the device with plug 640. Similarly, fluid inserted through portal 1640 of bottom endplate 1600 is sealed within the device by plug 1900.

One skilled in the art can see that any of the models described here, have many variations by incorporating a mix of features. For example, bottom endplate 600 can have a portal 1640 that seals with plug 1900. As another example, the various RJS described here can also have the line features 1801 and 1801. To further illustrate this point, a device could have top endplate 1500 and bottom endplate 600.

Figure 8:
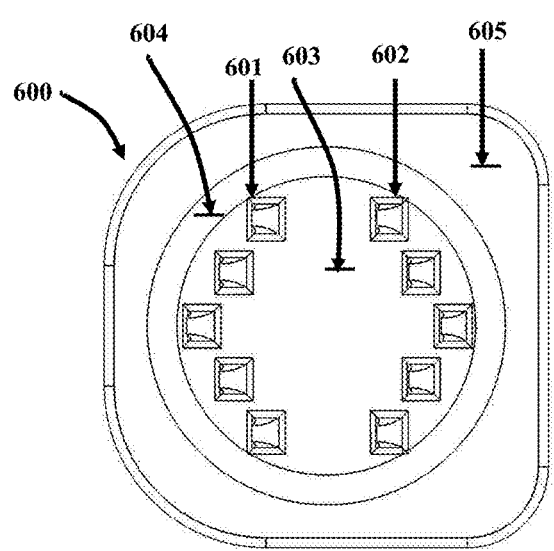
FIG. 8 provides a drawing of the inferior surface of a bottom endplate 600 of the NFS-1 device according to the invention.

Those skilled in the art will appreciate that various alternate geometries of elements of the NFS-1 device according to this invention may be utilized, without departing from the essence of the invention disclosed herein and as defined by the claims. FIG. 8 presents a bottom view of bottom endplate 600, showing multiple curvate surfaces designed to fit into a cavity within the superior surface of an inferior vertebra of an FSU. In the embodiment shown in FIG. 8, a central surface of the bottom endplate 600 comprises a spherical section 603 to match the area of cancellous bone present at the superior surface of an inferior vertebra of an FSU.

Figure 9:
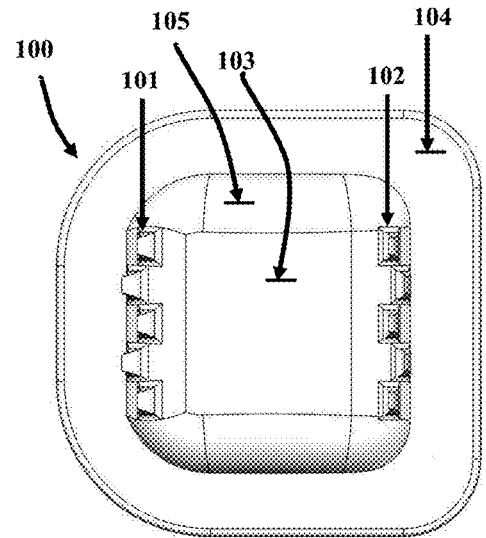
FIG. 9 provides a drawing of the superior surface of a top endplate 100 of the NFS-1 device according to the invention.
Figure 12:
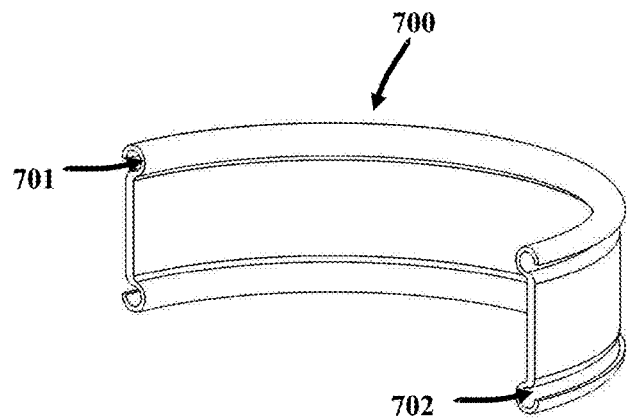
FIG. 12 illustrates a section view of a particular embodiment of the sheath component 700 of the NFS-1 device according to the invention. Raceways 701 and 702 accommodate sheath retaining rings 801 and 802 of FIG. 13, respectively.
Figure 13:
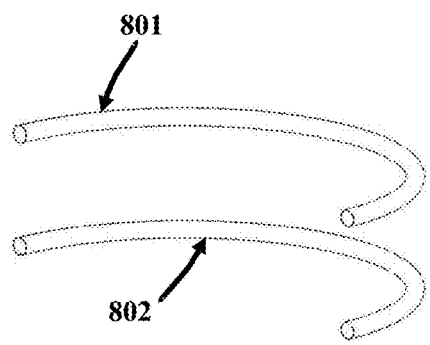
FIG. 13 demonstrates a section view of a particular embodiment of the sheath retaining rings components 801 and 802 of the NFS-1 device according to the invention.

FIG. 9, shows an top view of top endplate 100, again showing multiple curvate surfaces designed to fit into a cavity in the inferior surface of a superior vertebra of an FSU. In this embodiment, a central surface comprises a cylindrical section 103. FIG. 11 shows an elevational perspective view of an embodiment of nucleus 400. FIG. 12 provides a view of a portion of sheath 700, while FIG. 13 shows a view of a portion of the sheath retaining rings 801 and 802. Those skilled in the art will appreciate that alternate embodiments and geometries for each of these features as suggested by these exemplary embodiments may be employed while remaining within the scope of the present invention.

FIGS. 21 through 27 illustrate a snap-fit embodiment D3 with top endplate 1500 with a spherical section dome top 1510 and spherically arranged fixation teeth 1520 and 1530; a bottom endplate 1600 with a spherical section dome undersurface 1610 and spherically arranged fixation teeth 1620 and 1630; a circular bottom endplate cavity 1610; a retainer 1650 integrated with 1600; nucleus 2100, whose lip intersects surface features 1801 and 1803 in a planar curve; circular cushion ring 1700; and an RJS 1800 integrated with the bottom endplate.

Figure 14:
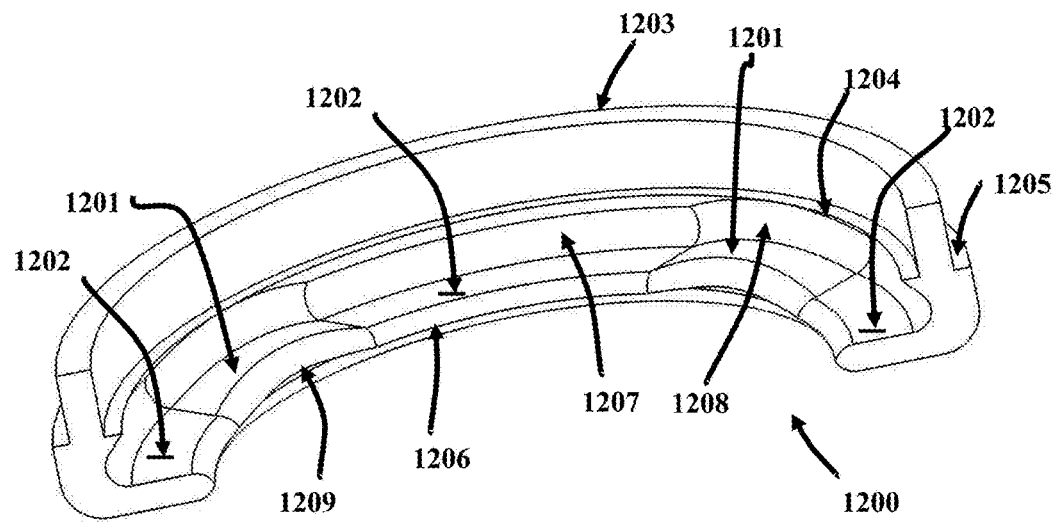
FIG. 14 depicts a sectional view of an embodiment 1200 of the Ring-Joint-Stop, RJS, a component of the NFS-1 device according to the invention.

FIG. 14 presents a view of an RJS according to this invention with an enhanced Range-Of-Motion (ROM). Four cylindrical surfaces 1201, whose axes of rotation pass through the center of curvature of the ball-and-socket joint, located at the four quadrant points (half of the anterior spherical section and all of the right-lateral section are depicted in FIG. 14), are created by an approximately 40° rotation about the z-axis (anterior/posterior quadrant) and by an approximately 40° rotation about the x-axis (left-lateral/right-lateral quadrant) of the reference frame in the neutral position. These four cylindrical surfaces 1201 allow equal ROM for FE and LB rotations. The four concave curvate surfaces 1207 and the four concave curvate surfaces 1208 all intersect, at first contact, the convex curvate nucleus dome lip 406 in a curvate line at any location whereat the RJS engages nucleus dome lip 406. As the contact force increases, dome lip 406 compresses somewhat and the contact morphs into a small area. Contact occurs when either FE and LB exceeds α degrees. Rim 1206 also engages the core 402 during such contact. The type of contact, morphing from a line to a small area, depends upon the amount of expansion of the core 402 and the contact forces tending to compress the core. Surfaces 1202 are flat and contact the flat, ring shape undercut 409 of the dome lip 406 when the FSU is driven to extremal angles by the spinal muscles or other external forces. This contact, again, can morph from a line to a small area due to the flexibility of the dome features under stress. Preferably, in this embodiment, there is a smooth integration and transition between cylindrical sections 1201 and the flat surfaces 1202. The four ring sections 1202 between the four cylindrical surfaces 1201 maintain the strength and stiffness of the RJS.

In an NFS-1NSF embodiment, stem 1203 is press-fit, laser-welded, or both, into a compatible raceway. In such an embodiment, a split RJS is employed such as that shown herein above. Shelves 1204 and 1205 allow more careful control of the press-fit by serving as limiting stops during press fit insertion. Further, edges of 1203 can be chamfered to facilitate insertion, as with the RJS in FIG. 6.

A top endplate, employing an RJS as shown in FIG. 14, wherein the bearings 1201 have been designed to permit the Flexion/Extension ROM of the top endplate to equal ±10° (rotation about the x-axis); its Lateral Bending ROM to equal ±10° (rotations about the z-axis); and no constraints on axial rotation. Combinations of the three simultaneous rotational motions, namely, Flexion/Extension, Axial rotations and Lateral Bending, while all nominally within their neutral ROM, can lead to situations where the net motion exceeds the limits permitted by the RJS, namely, when the top endplate would force a configuration of the top endplate that would impinge the retainer plate. Constructively, such a motion is equivalent to a rotation about some axis k in the zx-plane of the nucleus that exceeds ±10°. This motion will be opposed by the RJS interacting with the nucleus lip and the cushion ring.

Interestingly, the condition just mention cannot happen when Lateral Bending does not exceed ±6.7°. Since a Cervical Functional Spinal Units (CFSU) of a human body, on average, restricts Lateral Bending to ±6.5°, the RJS in FIG. 14 will allow three nominal simultaneous rotation motions of of the top endplate without restricting the motion. For example, from C2-C3 on down to C6-C7, a top endplate rotation comprising: Flexion=10°, Axial Rotation=10° (typically restricted by the body to be less than 10°), and Lateral Bending=6.7° (typically restricted by the body to be less than 6.7°) will be accommodate by the device without the RJS interfering in the motion.

Many everyday cervical rotations, as mentioned in the previous paragraphs, will fall within the ROM specified above for the RJS of FIG. 14, namely, FE and LB rotations will not be at the limit α. Such rotations will not generate contact between dome features 409 (FIG. 3B), 406, and core 402 with four each of the following RJS features: curved surfaces 1201 (cylindrical convex), 1207 (spherical concave), 1208 (spherical concave), surfaces 1202 (planar), rims 1209, and rims 1206. Hence, many cervical motions do not cause wear between these elements during operation.

Concave spherical surfaces 1207 and rims 1206 do not normally contact elements of the nucleus 400 within the ROMs specified above, including the extremal positions thereof. Rotations outside of the normal ROMs can, however, cause such contact. This is where the circular and rounded-corners-square (rcsq) cushions come into play, which will be further described herein below.

In a further embodiment according to this invention, a modified RJS embodiment is incorporated into the NFS-1 device such that lateral bending and flexion-extension is independent of any other motion. This is accomplished, as described below, with reference to FIGS. 16 and 17.

Figure 17:
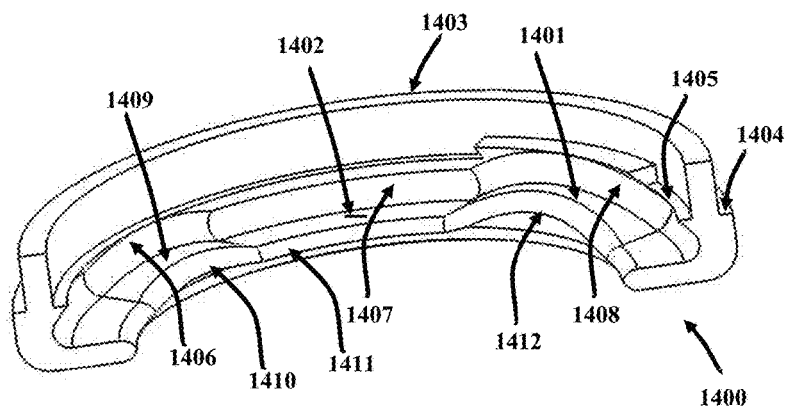
FIG. 17 yields a sectional view of a preferred embodiment 1400 of a Ring-Joint-Stop, a component of the NFS-1 device according to the invention.

FIG. 17 shows a section view of an RJS 1400. A non-snap-fit embodiment of RJS 1400 is divided into anterior and posterior elements in the same manner as RJS 300 and RJS 200, respectively. These split elements of RJS 1400 are not explicitly shown here. However, stem element 1403 with insertion stops 1404 and 1405 apply only to the non-snap-fit embodiment of the RJS 1400. For a snap-fit embodiment of RJS 1400, these elements no longer pertain, and the RJS 1400 comprises an integrated structure with the top endplate.

Convex cylindrical surfaces 1401 and 1409 are generated by rotations about the x-axis and z-axis, respectively, where those axes pass through the center of curvature of the spherical section of the nucleus dome 401.

Boundary edges 1410, 1411, and 1412 smoothly transition to one another. There are four sections 1411 and two each of 1410 and 1412. An zx-plane projection of these edges generates a circular boundary in a preferred environment. Other boundary shapes are not precluded. These eight curvate edge segments and the spherical concave surfaces 1406, 1407, and 1408, as well as flat surface 1402, all have critical dimension for proper functioning of the RJS 1400.

Figures 15, 16:
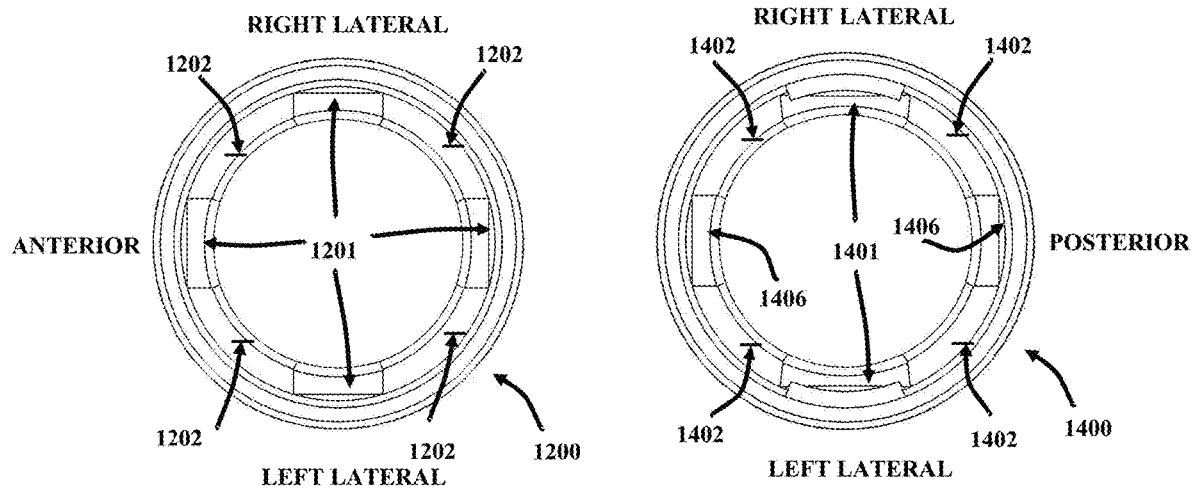
FIG. 15 illustrates a top view looking down into the embodiment 1200 of the Ring-Joint-Stop (RJS) shown in FIG. 14, a component of the NFS-1 device according to the invention.
FIG. 16 presents a top view looking down into the embodiment 1400 of the Ring-Joint-Stop (RJS) shown in FIG. 17, a component of the NFS-1 device according to the invention.

The RJS 1400 differs from RJS 1200 (FIG. 14) in that the former can set different angle limits $\alpha$ and $\beta$ for flexion-extension (FE) and lateral bending (LB), while the latter sets a single angle limit for both. To make the following discussion clear, the four cylindrical angle control elements 1201 of RJS 1200 are identified as anterior 1201.A, 1201.P, 1201.L, 1201.R, where A stands for anterior, P for posterior, L for left-lateral, R for right-lateral. The anatomical positions are indicated in FIGS. 15 and 16. The two cylindrical angle control elements 1406 and the two cylindrical angle control elements 1401 of RJS 1400 are likewise identified by their anatomical position, namely, 1406.A, 1406.P, 1401.L, 1401.R, respectively. For both RJS 1200 and RJS 1400, the anterior and posterior angle control elements 1201.A, 1201.P and 1406.A, 1406.P, respectively, allow uninhibited lateral-bending (LB) along their cylindrical surfaces, which share the same central axis, namely, the z-axis passing through the ball-and-joint spherical rotation center. These same angle control elements, however, limit the flexion-extension (FE) to $\alpha$ degrees. On the other hand, 1201.L, 1201.R and 1401.L, 1401.R, respectively, allow uninhibited flexion-extension (FE) along their cylindrical surfaces, which share the same central axis, namely, the x-axis passing through the ball-and-joint spherical rotation center. However, angle control elements 1201.L, 1201.R limit lateral bending (LB) to $\alpha$ degrees whereas angle control elements 1401.L, 1401.R can be arrange to limit lateral bending to $\beta$ degrees, where $\beta \leq \alpha$. The choice of a practical range of values for this invention is discussed below.

In the literature flexion-extension FE ROM is listed as the sum of both flexion and extension movements. Hence, −10° to +10° FE in the context of this instruction would be restated as a 20° ROM in the literature, or 2·$\alpha$. Also, lateral bending (LB) is usually specified as one side only, assuming by symmetry the other side is the same. In the context of this instruction, LB for the RJS 1200 is $\alpha$ degrees and that for the RJS 1400 is $\beta$ degrees. Various embodiments of this invention can accommodate most of the FE and LB ROMs reported in the literature. Therefore, in this age of 3D manufacturing, a particular embodiment of the invention can be manufactured to suit client requirements. For example, the maximum mean values reported in "Panjabi and White, *Clinical Biomechanics of the Spine, 2$^{nd}$ Addition*, Lippen-cottt-Raven, Pub., 1990, p110" for the cervical spine below $C_0$-$C_1$ are, for the five studies reported for FE, 2·$\alpha$=23°, which occurred in one study for $C_5$-$C_6$. For the four studies reported there for LB, $\ominus$=11°, which also occurred in one study for $C_3$-$C_4$ and $C_4$-$C_5$. This invention can be embodied to accommodate all reported mean value ROMs, except the outliers mentioned, for all levels of the cervical spine below $C_0$-$C_1$, since 2·$\alpha$=20° and, $\beta$=11° is manufacturable for this invention. Not only can the invention realize the ROMs required, but it actually mechanically limits the range allowed with a soft joint stop produced by the RJS and cushion rings, soft because at the stop, where contact of the RJS with elements of the nucleus occurs, the flexibility of the nucleus and the compressibility of the cushion ring still permits further motion, but with greater and greater resistance. As mentioned previously, it may be desirable for the RJS to engage the cushion ring before the nucleus lip as the former is able to take more force. For example, for ROM of a the cushion thickness could be changed to engage the RJS at $\alpha$−2°. To work for $\beta$ as well would require a cushion ring with larger thicknesses along the lateral sides for a few degrees which then flattens out towards the anterior and posterior regions. In this case, the cushion ring must be fastened to the retainer plate by means of a biocompatible adhesive, such as a biocompatible polyurethane adhesive, or by mechanical means, for example, through snap attachment, or by a combination of means. Alternatively, the PCU cushion ring itself can be adhered to a roughened upper surface of the retainer by heat treatment with the retainer so that the PCU lower surface melts into the retainer plate roughened surface to form an extremely durable, biocompatible bond.

As a result of inclusion of this embodiment of the RJS in the NFS-1 device, whether as a unitary component of the top endplate for snap-fitting of the nucleus, or as separate components to be assembled with the top endplate, the following practical range for ROM's of a cervical disc prosthesis can be chosen for implementation.

Those skilled in the art will further appreciate that the ring-joint-stop with a continuous, circular raceway may be defined by geometries other than a circular raceway. An elliptical or other regular quadratic curve may be employed. Those skilled in the art of kinematics are enabled by the present disclosure to define variations to the shape of the raceway component without departing from the heart of the presently disclosed invention.

Figure 29:
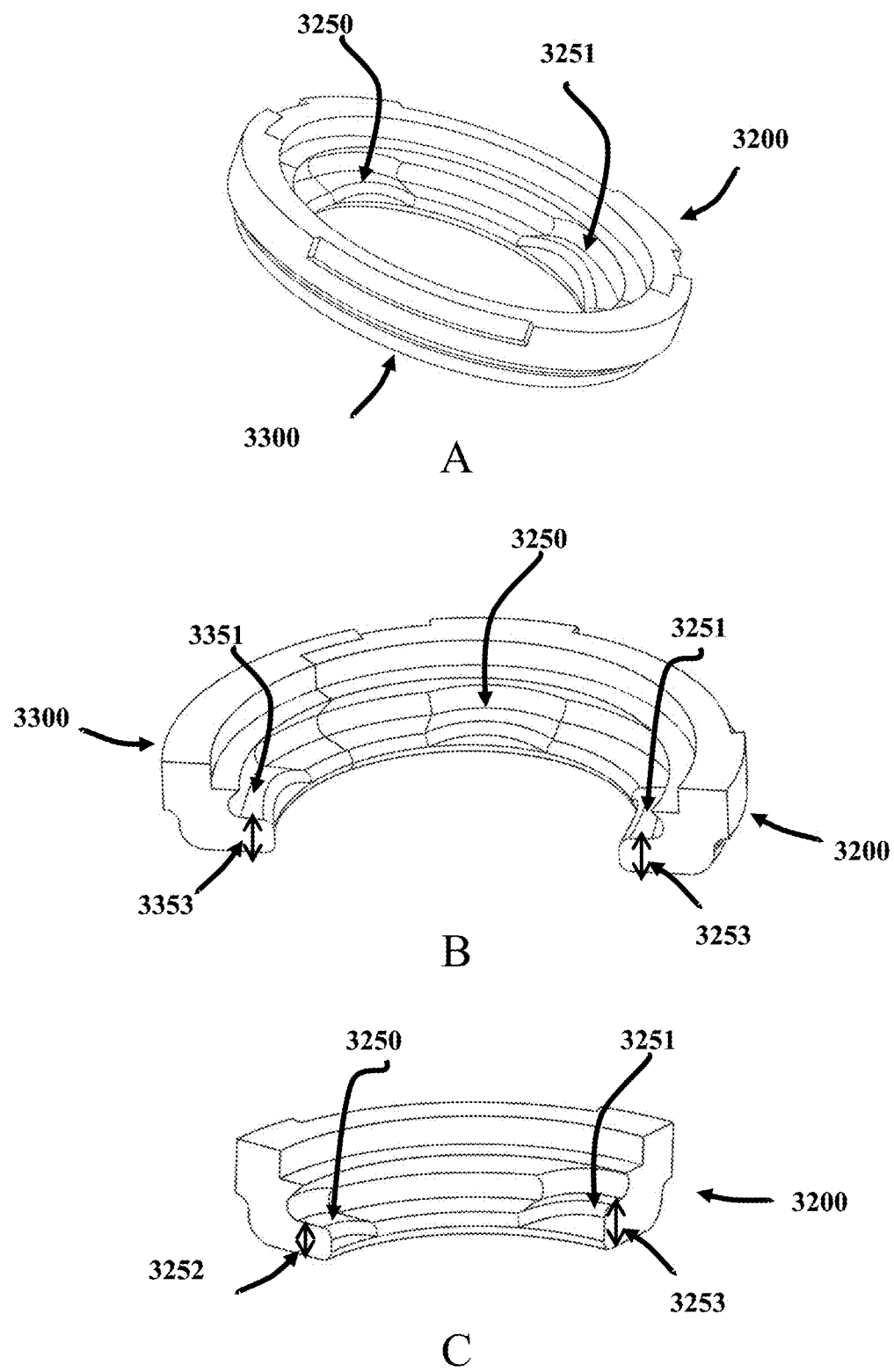
FIG. 29 provides a representation of an exemplary embodiment of the invention in which, in FIG. 29A, a complete Ring-Joint-Stop (RJS) is provided with two segments (3300 and 3200) the latter showing curvate posterior bearing element (3250) and curvate left-lateral bearing element (3251)

With reference to FIG. 29, a representation of an exemplary embodiment of the invention is provided in which, in FIG. 29A, a complete Ring-Joint-Stop (RJS) is provided with two segments 3300 and 3200 the latter showing curvate posterior bearing element 3250 and curvate left-lateral bearing element 3251; FIG. 29B shows a tilted, frontal-section view, revealing curvate right-lateral bearing element 3351 and curvate left-lateral bearing 3251 as well as a curvate posterior bearing element 3250, with curvate anterior bearing element 3350, not shown, opposite 3250; FIG. 29C, shows a half-quadrant of 3200, illustrating the difference in the maximum height of the two bearings: maximum height 3252 for curvate posterior bearings 3250, and maximum height 3253 for curvate left-lateral bearings (3251), while, similarly, a maximum height for curvate anterior bearing 3350 not shown, is 3352, also not shown) and maximum height for curvate right-lateral bearing 3351, designated by 3353, is revealed in FIG. 29B.

The Ring-Joint-Stop (RJS) in FIG. 29 controls the ROM of Flexion-Extension (x-axis rotation) defining angular parameters $\alpha_1$ and $\alpha_2$, and Right-Left Lateral Bending (z-axis rotations) by angle parameters $\beta_1$ and $\beta_2$. Axial rotations (y-axis), may be constrained, or unconstrained, when executed, depending upon the orientation of the top endplate on the nucleus dome.

Angle parameters $\alpha_1$ and $\alpha_2$ determine the maximum heights 3252 and 3352 (not shown) of posterior and anterior curvate bearing elements, 3250 and 3350 (note shown) respectively, and, consequently the ROM enforced by the RJS for Flexion and Extension, respectively. Note: curvate posterior bearing limits Flexion and curvate anterior bearing limits Extension.

Angle parameters $\beta_1$ and $\beta_2$ determine the maximum heights 3253 and 3353 of left-lateral and right-lateral curvate bearing elements, 3251 and 3351, respectively, and, consequently the ROM enforced by the RJS for right-lateral bending and left-lateral bending, respectively. Note: curvate left-lateral bearing limits Right-Lateral Bending and curvate right-lateral bearing limits Left-Lateral Bending.

While, as discussed extensively herein above, where $\alpha=\alpha_1=\alpha_2=\beta_1=\beta_2$, in this embodiment, the ROM of Flexion-Extension angle X (x-axis rotation) is now constrained such that $-\alpha_2 \leq \lambda \leq \alpha_1$, and, the ROM for Right-Left Lateral Bending angle $\mu$ (z-axis rotation) is now constrained such that $-\beta_2 \leq \mu \leq \beta_1$. This allows independent, mechanical specification of the limits for each of the angles: Flexion ($\alpha_1$), Extension ($\alpha_2$), Right-Lateral Bending ($\beta_1$), and Left-Lateral Bending ($\beta_2$). For any complex rotation of the top endplate that results in any of these limits being exceeded, the RJS will engage the lip of nucleus dome and provide a soft stop.

As a result, in this embodiment of the invention, the device includes a top endplate which comprises or is assembled to comprise a curvate Ring-Joint-Stop (RJS), which, itself, includes:

i. raised left and right lateral convex cylindrical bearing surfaces which define two angle parameters ($\beta_1$ and $\beta_2$, respectively), within a Ring-Joint-Stop raceway, generated by rotating curvate surfaces of same or different sizes about an x-axis that passes through the center of curvature of said first joint (ball-and-socket), which dictates the ROM of Right-Left Lateral-Bending angle $\mu$ such that $-\beta_2 \leq \mu \leq \beta_1$;

ii. raised posterior and anterior convex cylindrical bearing surfaces which define two angle parameters ($\alpha_1$ and $\alpha_2$) within a Ring-Joint-Stop raceway, generated by rotating curvate surfaces of same or different sizes about a z-axis that passes through the center of curvature of said first joint (ball-and-socket), which dictates the ROM of Flexion-Extension angle $\lambda$ such that $-\alpha_2 \leq \lambda \leq \alpha_1$; and iii. four cylindrical bearing surfaces in which at least one surface contacts a curvate nucleus dome lip in a curvate line for any rotation angle outside the ROM of either Flexion-Extension or Lateral-Bending, such that, as the rotation angle increases, contact forces increase; and either iva. a Ring-Joint-Stop rim, smoothly integrated with and transitioning between each of said four cylindrical bearing surfaces and four, substantially flat, inner-raceway surfaces, wherein said four substantially flat, inner-raceway surfaces provide strength and stiffness to said Ring-Joint-Stop; or ivb. a Ring-Joint-Stop rim, which, with respect to the nucleus x-y-z frame of reference and with all four angle parameters equal the same value $\alpha$, that facilitates and limits the ROM of both Flexion-Extension angle ($\lambda$) and Lateral Bending angle ($\mu$) within the range $-\alpha \leq \lambda$, $\mu \leq \alpha$, as follows:

a) it allows any sequence of rotations, that at no time results in an equivalent rotation that would require, as part of its implementation, a rotation about some axis in the x-z plane whose magnitude is greater than $\alpha$ degrees;

b) it permits any sequence of rotations satisfying a), which includes Axial (y-axis) rotations, then such Axial rotations move without constraint, whereas any Axial rotation in a sequence of rotations that does not satisfy condition a), is constrained by the RJS;

c) it constrains a sequence of rotation motions that does not satisfy condition a) by contacting a cushion ring included in said device so as to protect the RJS and a retainer plate from impingement damage that would be caused by rotations exceeding either Flexion-Extension or Lateral-Bending Ranges-of-Motion (ROMs), and, by resisting further motion once the RJS contacts the cushion ring, such that said engagement of the RJS and cushion ring provides a soft stop with increasing resistance as the angle increases beyond $\alpha$ degrees, eventually producing a hard stop; and d) it comprises a curvate or conic shaped underside portion which participates in resisting either out-of-range, or near out-of-range rotations through curvate line or linear contact, respectively, with a cushion ring thickness designed for such contact.

In an embodiment in which a cushion ring is included, in an embodiment thereof, it is adhered, for example, with an adhesive or by any other known mechanical attachment, to the RJS itself, then it would move with the top endplate and could then be used for the four independent angles as follows: the RJS cushion ring thickness under each particular bearing causes the RJS to engage the retainer plate cushion ring at the specified angle.

It will be appreciated that, with respect to the Ring-Joint-Stop rim, alternate embodiments are provided in which, in alternate embodiment (iva): the RJS starts to engage the cushion ring for one specific angle of the four angle parameters; e.g. if the cushion ring is thick enough to engage with the RJS for the smallest angle, it would engage it first and continue to engage for all the others, even though their limits have not been reached; whereas, in alternate embodiment (ivb) the cushion ring thickness is such that it will only engage the RJS rotating through the largest permissible angle, will not engage the RJS for any of the smaller angles, even if they are out of range.

From the present disclosure, those skilled in the art will appreciate that the NFS-1 device according to this invention may have applications in human and non-human animals. Likewise, the device may have applications in non-living subjects, as in, for example, robotic applications.

Further, from the present disclosure, those skilled in the art will appreciate that the nucleus component of the NFS-1 device according to this invention may be manufactured by 3D printing methods, including with living tissue, by production of a collagenous biological matrix, or based on stem cell technologies.

EXAMPLES

Those skilled in the art, based on the present disclosure, are enabled to make and use the NFS-1 implant according to this invention. The following exemplary considerations are provided to further describe and enable manufacture and use the device, as an additional but non-limiting guide to those skilled in the art. The specifics of these examples are not, however, intended to limit the scope of the invention. Rather, the scope of the invention should be ascertained by reference to the complete disclosure and the claims, including equivalents thereof.

Example 1

Load And Deformation Considerations for the NFS-1 Device According to This Invention When Implanted Into a Living Recipient as a Motion Preserving Replacement of a Defective Intervertebral Disc For purposes of exemplification, the area of the spherical section of the nucleus in a preferred embodiment is defined as about 48.66 mm². Assuming a force F=486.6 N is exerted at the top endplate, such force is distributed across the spherical section concavity present in the underside of the top endplate, since at such load, where a titanium endplate is utilized, the top endplate remains substantially rigid. Accordingly, the pressure experienced by the Nucleus is: 486.6 N/48. 66 mm²=10 MPa. At 10 MPa, depending on the composition of the nucleus, a compression of about 10% is experienced. The height of the nucleus, from the top of the bottom endplate to the top of the top endplate spherical concavity is preferably about 4.8 mm. Thus, a 10% compression causes the height of the nucleus to be reduced by about 0.48 mm. At such a pressure, which exceeds normal loading by more than a factor of 2, slight impingement (contact and load) would be experienced between aspects of the top and bottom endplates, but only at the extremal FE and LB angles. The strain that results in a gap g=0.4 mm in a preferred embodiment is 0.4/4.8=1/12=0.083. A stress-strain curve predicts a strain for this displacement of approximately 8 MPa, which translates to a force F=48.66 mm²×8 MPa=48.66×8 N=389.28N. It would be extremely rare for such a force to be observed, and would be completely outside normal operating loads, which are typically limited to no more than about 150N to 200N. In light of these considerations, those skilled in the art will appreciate that in general, except in extremely rare circumstances in which super-physiological loads are experienced by a subject's spinal column, impingement is unlikely to ever occur, and if it were to occur, it would limit undesired compression at the motion segment where implanted, while significant damage at other purely biological segments would likely be severe.

By contrast, however, the nucleus, depending on the specifics of its composition, would be expected to deform somewhat under a constant load over a long period of time post-implantation. Those skilled in the art will appreciate that extent of such deformation under "body-wet" and "body-temperature" conditions would need to be carefully and repeatedly experimentally verified. Nonetheless, from appropriate compression curves for a preferred composition of the nucleus according to this invention, it is possible to estimate that under a force of 150N, distributed over the nucleus upper surface, would result in a strain of:

$$150N/48.\ 66\ mm^2 = 3.08\ MPa$$

Reading from an appropriate stress-strain curve for such preferred composition, a compression strain of about $s_c$=3.5% is predicted. Hence, under a long-term average load of 150N, the nucleus would be expected to deform less than $$0.035 \times 4.8\ mm = 0.168\ mm$$

It is believed that in fact, this over-estimates the anticipated extent of deformation since a strain of 3.5% is well within the linear range of the preferred composition of the nucleus according to this invention. Whatever degree of deformation is induced by such force, it is predictable that such deformation would not be result in permanent deformation.

Example 2

Surface Area and Load Considerations for the NFS-1 Device According to This Invention When Implanted Into a Living Recipient as a Motion Preserving Replacement of a Defective Intervertebral Disc In a preferred embodiment, the surface area of the dome of the nucleus is about 50 mm². In such an embodiment, a 500N load, approximately 3.3 times maximum cervical spinal loading of 150N and 10 times the load of the human head (~5 Kg), produces a stress of about 10 MPa on the dome surface and will compress a particular 6 mm PCU candidate only 10% or 0.6 mm in the neutral position. A gap 907 of about 1 mm is expected to protect against impingement of the RJS 200 or 300 with the retainer 500 except in extreme circumstances Similar claims apply to RJS 1200 and RJS 1400. According to Moroney et al (J. Biomechanics, 21(9): 767,1988) the stiffness coefficient of a cervical disc is 500N/mm. Thus, a disc compression of only about 1 mm is anticipated to result from a load of 500N.

Example 3

Range of Motion and Gaps Provided in the NFS-1 Device to Accommodate Such Motions In an exemplary embodiment according to this invention, the motion of the top endplate, riding on the nucleus spherical section is defined by the ring-joint-stop raceway, which can allow rotations up to approximately ten degrees (10°) about any axis at the center-of-rotation and perpendicular to the central axis of the nucleus. Furthermore, in a preferred embodiment, the distance between the top and bottom plate at any extremal rotation, permitted in relation to each other, is slightly larger than about 0.4 mm. The 0.4 mm is a consequence of specific geometry of one embodiment of the device according to this invention. Those skilled in the art will appreciate that while 0.4 mm is mentioned here as a specific value of the gap between any portion of the top plate and any portion of the bottom plate, for particular subjects, and depending on the particular level at which intervertebral disc replacement is required, the gap may be as small as about 0.3 mm and as large as 0.5 mm, with every intermediate gap being accommodated by appropriate adjustments in either the ring-joint stop circular raceway dimensions, the dimensions of the nucleus lip interface, or both, each of which constrains the minimum gap distance between the top and bottom endplates in relation to each other. In an embodiment where the raceway is circular, the minimum gap distance remains constant. Those skilled in the art will appreciate that an elliptical or other smooth raceway curve may be employed such that the minimum gap distance is not constant as may be required in any given subject or intervertebral disc replacement. Also, for RJS 1400 the gap will be larger for lateral bending than flexion-extension, since the limit for LB rotations is less to accommodate natural physiologic motion more closely.

Example 4

Further Exemplary Embodiments and Considerations in the Manufacture and Use of the NFS-1 Device According to this Invention The NFS-1 device according to this invention is implanted via appropriate insertion procedures and hardware into a space in the cervical or lumbar spine between adjacent (superior and inferior) vertebrae, after removal of intervertebral tissue, (including, e.g. the intervertebral disc tissue and any bone material removed from the underside of the superior vertebral body or the top surface of the inferior vertebral body), to securely accommodate insertion of the device. The direction of insertion is to be obeyed, whether an anterior, posterior or oblique approach is adopted for implant insertion. This is dictated by the orientation of retaining "teeth" which "bite" into the bone surface once the implant is correctly emplaced into the intervertebral space and any distraction is released so that the superior and inferior vertebral surfaces are allowed to impinge on the device. The inclusion of such retaining teeth is not absolutely required, on either the top or bottom endplates. However, to avoid the need for retaining hardware post-insertion, inclusion of such retaining teeth or equivalents thereof, is preferred.

Accordingly, where, e.g. the device is implanted into the cervical spine from an anterior approach, following appropriate distraction of the appropriately cleaned and shaped intervertebral space, the device is gripped by an appropriately shaped gripping tool, which preferably retains the device and its internal feature in a firm vertical orientation. Upon release of distraction, the retaining teeth on the top endplate and bottom endplate bite into the superior and inferior vertebral bodies, respectively, preventing any tendency for the device to "back out" of its implant location. When so implanted, from an anterior approach, the recipient in need of such treatment would have the left side of the implant oriented toward the recipient's left shoulder, the right side of the implant oriented toward the recipient's right shoulder, the anterior side would be oriented outward in the same direction as the recipient's gaze, and posterior side would be oriented toward the recipient's back.

The top endplate and the bottom endplate can each preferably be manufactured by any number of different processes from any number of different materials, including but not limited to:

(a) titanium, stainless steel, cobalt chromium alloy (Co-CrMo), or other metals or metal alloys known in the art or which hereafter come to be known as being appropriate for this purpose, any of which may be textured or sprayed with titanium plasma or another known treatment, including optional coating with hydroxyapatite or any other material which encourages bony in-growth; processes known in the art, including molding, three-dimensional printing (3DP), machining, or any other manner of manufacture appropriate for production of the top and bottom endplates are contemplated herein;

(b) biological material, whether derived from, e.g. cadaveric tissue or synthetic, e.g. from growth or 3DP in a laboratory, including where e.g. bioglass or like material or bone growth factors or the like is/are incorporated, wherein said biological material exhibits sufficient structural integrity to perform the function of the endplate (engagement with the lower surface of a superior vertebral body or engagement with the upper surface of an inferior vertebral body, while at the same time providing a coherent mechanism to provide structural support and containment of the remaining components of the device). Where mating surfaces exist, as discussed below, non-lubricious surfaces, e.g. bone, may be protected by a lubricious surface comprising e.g. polished metal, plastic, or other polymeric material, e.g. ultra-high molecular weight polyethylene.

Those skilled in the art will appreciate that the term "lubricious" and its variants, such as "lubriciously", as used in this disclosure, means with respect to mating surfaces that such surfaces contact each other with the lowest possible coefficient of friction. Accordingly, highly polished metal surfaces, highly polished metal to extremely smooth polymer surfaces, and extremely smooth polymer to polymer contact surfaces are implied by these terms. In addition, when such mating surfaces are required to be lubricious, the device according to this invention provides for inclusion of a biologically compatible (i.e. non-toxic, durable and retainable) fluid such, as hyaluronic acid, chondroitin, polymeric and other substances as are known in the art or which hereinafter come to be known as useful in providing such functions, by providing a fluid access port and plug. The plug may be press-fit into the port, or it may be screw-fit in which case appropriate mating threads are provided as between the port and port plug surfaces. A Phillips' head, flat head, Allen wrench driven or like purchase providing structure is optionally provided in the head of the plug, to assist in insertion thereof.

Those skilled in the art will appreciate that many different device sterilization techniques are known in the art. Preferably, the device according to this invention is provided to a surgeon in a fully assembled state, ready for implantation into the spine of a living vertebrate, preferably a primate, and most preferably a human. In such a sterile state, depending on the sterilization technique employed, (e.g. autoclave treatment known in the art) it may be necessary to add the lubricious fluid post-sterilization, via the fluid access port, described above. Alternate sterilization techniques, (e.g. ethylene oxide) may be used to prepare the fully assembled device, including fluid already added via the fluid access port, which is itself sterile, sealing the fluid access port, and storing the device in an impervious, sealed container filled with appropriate levels of ethylene oxide, known in the art for this purpose. In any event, in a preferred embodiment, the device is provided in a sterile, sealed container. In an alternative embodiment, partially assembled components of the device may be separately sealed in sterile containers. A kit may be provided for snap-fitting together a fully assembled device, by providing appropriate component parts, each of which is provided in a sterile or non-sterile condition, for assembly and sterilization.

The top endplate and the bottom endplate are preferably manufactured from similar materials and by similar processes, but this is not an absolute requirement for all embodiments of the invention. Permutations and combinations of disclosed elements are produced to advantage, given appropriate resources and demands. Differently dimensioned implants according to this invention are preferably provided for differently aged recipients (with all features scaled downward, appropriately, the younger the recipient), and based on the location in the spine where implanted. In at least a first commercial embodiment of the NFS-1 disc, for manufacturing ease and consistency of product, both top and bottom endplates are preferably molded, machined, or 3D printed metal, including but not limited to, e.g., titanium, or metal composite, e.g. CoCrMo.

The top endplate includes a raised section dimensioned and shaped for optimal engagement with the lower surface of superior vertebral body. In this embodiment according to this example, a raised, substantially rectangular surface, with a substantially flat top aspect of smaller rectangular dimension than the base of the raised rectangular feature is used. Posterior and anterior rows of retaining teeth are included. All edges on all surfaces are chamfered or rounded so as to reduce stress on the device or recipient tissue during implantation.

The intermediate section comprising a sheath, lower and upper sheath retainer rings, and a nucleus. The sheath is composed of a flexible, biologically compatible, durable, fluid and cell impermeable material to prevent migration of materials into the internal workings of the device, which could in time calcify or otherwise compromise the internal workings of the device. Those skilled in the biological and material science arts will know which materials would be appropriate for this purpose. For example, the sheath material may be composed of a flexible metal sheath, polymer, or biological material, such as collagen. The lower and upper sheath retainer rings are composed of flexible and resilient material which, once emplaced within a groove provided in the upper and lower plates provided for that purpose, tightly constrain the sheath to remain in position surrounding the intermediate section of the device. Metallic rings, including rings with a hinge or discontinuity, or flexible but durable rubber, plastic, polymeric or like material, including heat shrinkable material, are known in the art and may be selected by those skilled in the art for this purpose.

The nucleus is composed of a semi-rigid but partially compressible material, adequate to provide at least the following functions: a mating ball and socket joint about which the top endplate is lubriciously rotatable in any direction, within limits defined by the remainder of the geometry of the device; shock absorption to sustain compressive forces applied via downward compression of the upper endplate or via upward compression via the bottom endplate. A wide range of materials now known or which hereinafter come to be known in the art, may be appropriate for this purpose. A wide range of commercial manufacturers are skilled at producing appropriate materials for this purpose. As noted herein above, DSM provides a wide range of materials for this purpose and are very skilled at adapting their product to provide desirable characteristics as described herein for the nucleus. For the present invention, it will be appreciated that it is important to select a material which has sufficient strength, over time, to sustain retention within the upper endplate joint, as described herein above, while at the same time having sufficient flexibility, including within the core portion of the nucleus, to sustain the torsional strains that, from time to time, may be imposed on the device once implanted into the intervertebral space.

In light of the foregoing disclosure and examples, those skilled in the art will appreciate and are enabled to practice the full range of claims provided herein. Included within the scope of this invention are at least the following embodiments:

A device comprising a top endplate engaged in a ball and socket configuration with a top dome portion of a nucleus to form a first joint of defined ranges of motion, a nucleus comprising a top dome portion, a core portion, and a bottom foot portion, and a bottom endplate translationally engaged with the bottom foot portion of the nucleus to form a second joint of defined ranges of motion. In such a device, the first joint and the second joint, in concert, when implanted into an intervertebral space, are constrained to facilitate substantially physiologically acceptable rotational, lateral and flexural motions, when compared with a biological disc in the spine of a recipient which said device is implanted to replace. Preferably, but not exclusively, the biological disc in the spine of a recipient in which the device is implanted is a cervical disc, such that, when implanted, the device in association with adjacent vertebrae form a functional spinal unit.

Preferably, the top endplate comprises a top surface for engaging with the underside of a superior vertebral body, and a bottom endplate comprises a bottom surface for engaging with the top surface of an inferior vertebral body. Preferably, the nucleus comprises a curvate top "dome" portion, a core portion, connecting the curvate top dome portion to a substantially planar bottom "foot" portion, and the foot portion. It is further preferred that the nucleus including its dome, core and foot, are either unitary or are connected to each other to form a unitary nucleus. Said nucleus can be a single polymer or a mix of polymers that vary from dome to foot as suggested in Doty U.S. Pat. No. 9,308,101. In such a device, the dome of the nucleus is preferably retained in contact with a mating curvate top endplate undersurface, such that the first joint is a closed-profile joint. In addition, the foot of the nucleus is retained within a cavity in the bottom endplate in connection with which it is translationally engaged, such that the second joint is a closed profile joint. In such a device, it is preferred for the first joint and the second joint to each comprise a nucleus retention mechanism providing defined degrees of motion of the top endplate about the top dome portion of the nucleus, and the bottom endplate in relation to the bottom foot portion of the nucleus, such that each mechanism sustains, restrains, constrains, stabilizes, and/or guides the larger motions required to preserve normal mechanical motion of a spinal joint, while at the same time, the nucleus provides a flexion component to guide and restrain/constrain the finer motions reached at the extremes set by the mechanical motion preservation components. The components of such a device are assembled by either a snap-fit or a non-snap-fit method for associating the device components to each other.

Preferably, the device includes a sheath surrounding the nucleus. Preferably, the sheath surrounding the nucleus is retained in position by upper and a lower sheath retention ring, each of which binds a top aspect of the sheath to the top endplate and a bottom aspect of the sheath to the bottom endplate, respectively, to thereby securely and imperviously define a chamber about the nucleus. The sheath retention rings are preferably retained in raceways defined circumferentially about the top endplate and the bottom endplate, respectively. The sheath, preferably, comprises of a thin, extremely elastic, biocompatible material. Preferably, sterile fluid is included within the chamber delineated between the sheath, the top endplate, and the bottom endplate. During assembly, the fluid is incorporated during manufacture via a port provided in the bottom endplate or in the top endplate, and port is sealed by a removable or press-fit/laser-welded port plug.

The device of this invention, in a preferred embodiment, is comprised of a first joint comprising the top endplate which comprises a ring joint stop unitary with or assembled to become unitary with the top endplate, wherein the ring joint stop either comprises an orifice and a raceway, such that the top dome portion of the nucleus snap-fits through the orifice for rotational retention within the raceway; or an orifice and raceway are defined about the core portion of the nucleus and, once assembled thereabout, retains the dome portion from traversing through the orifice for rotational retention within the raceway. In such a device, the bottom endplate preferably comprises a nucleus lower foot portion retention plate unitary with or assembled to become unitary with the bottom endplate. The retention plate preferably either comprises an orifice through which the nucleus lower portion is snap-fit for retention within a cavity defined within the bottom endplate; or is assembled about a core portion of the nucleus to comprise an orifice with sufficiently small diameter that the bottom foot portion of the nucleus cannot traverse through the orifice.

In a further aspect of this embodiment of the invention, a cavity is defined within the bottom endplate which permits the nucleus lower portion to translate along a horizontal plane defined by a substantially planar lower internal surface of the bottom endplate. Alternatively, or in addition, the top endplate comprises a ring joint stop assembled about a middle portion of the nucleus of lower diameter than the top portion of the nucleus, such that following assembly about the nucleus, the ring joint stop is assembled with the top endplate to define a raceway within which the nucleus top portion is rotationally retained. In yet a further embodiment, the bottom endplate comprises a nucleus lower portion retention plate which is assembled about a portion of the nucleus narrower than an orifice defined through the retention plate, when assembled and affixed to the bottom endplate, but which is too narrow for the nucleus lower portion to pass through such that the nucleus lower portion is retained within a cavity defined within the bottom endplate.

Features of this device preferably include one or more of the following features:

(a) Axial rotation, in the second joint realized by the allowed relative motion between the lower surface of the foot and the upper surface of the bottom endplate, is unrestricted regardless of the position of the nucleus within the cavity in the bottom endplate, and wherein boundaries dictated by an opening in the bottom endplate nucleus retainer and cavity form an enclosing cavity within which the nucleus foot and portion of the nucleus core and, hence, the entire integrated nucleus, translates and axially rotates;

(b) Spherical mating of the nucleus dome and a mating concavity provided on the underside of the top endplate, which restricts translational motion in a plane, wherein flexibility of the nucleus permits y-axis compression-extension, such that, during compression of the nucleus, all three elements of the nucleus, dome, core, and foot, have space into which they expand, such that relative rigidity of the top endplate forces the expanded dome to retain the shape of a spherical section; and (c) X-z axis translations of the top endplate and spherically mated nucleus dome occur in concert. In a preferred embodiment, the device allows six independent motion degrees-of-freedom between the top endplate and the bottom endplate without separation of either the first spherical joint (ball-and-socket) or the second planar joint within the device either prior to or following device implantation, such that the device maintains functional and positional integrity throughout normal operation, including in zero gravity. The moving closed profile joint surfaces of the device allow large mechanical motions of rotation, compression, and translation, while flexibility of the nucleus allows small flexure motions for all degrees of freedom when any joint, whether rotational or translational, is at one or more joint stops. Preferably, in such an embodiment, a ring joint stop is created by mating together an anterior and a posterior ring joint stop component to thereby create an enclosing aperture, or orifice which is too narrow to allow the nucleus dome to pass through, results in an assembly by press-fit, laser weld, or both, into a raceway of the top endplate, including at least one element to limit axial rotation within the raceway. Limiting axial rotation of the ring-joint-stop within its raceway, more securely fixes the element and permits it to essentially prevent axial torsion that might loosen the fit during usage. In a further preferred embodiment, the top endplate comprises, or is assembled to comprise, a ring joint stop comprising four cylindrical surfaces whose axes of rotation pass through the center of curvature of the first, (ball-and-socket), joint, located at four quadrant points to allow equal range of motion for flexion/extension and lateral bending, and four concave curvate surfaces which intersect and contact the convex curvate nucleus dome lip in a curvate line, such that, as contact force increases, the dome lip compresses somewhat and the contact morphs into a small area. In such an embodiment, preferably, when contact occurs via either FE and LB exceeding $\alpha$ degrees, a rim of the RJS engages the nucleus core, such that, due to smooth integration and transition between cylindrical sections and the flat surfaces, said four ring sections between the four cylindrical surfaces maintain the strength and stiffness of the ring joint stop. In a preferred aspect of this embodiment, the following range of motion rotations are facilitated to be performed sequentially, in any order, with respect to the same frame of reference each time, namely, the x-y-z axes in the neutral position: Flexion/Extension ±10° (z-axis), lateral bending ±10° at (x-axis) at any flexion/extension angle within its range of motion; unlimited axial rotation (y-axis) for any flexion/extension or lateral-bending within their respective ranges of motion. In a highly preferred embodiment, the ring joint stop accommodates lateral bending and flexion-extension independent of any other motion via a single angle limit. The device according to this invention preferably includes a nucleus top dome portion comprising a substantially convex top surface shaped to lubriciously mate with the underside of the top endplate and a bottom surface shaped to lubriciously and translationally mate with the bottom endplate such that the top and bottom endplates, once mated with the resilient nucleus, requires super-physiologic force to disengage from each other.

The invention further includes a method for total disc replacement which includes removing a damaged intervertebral disc to create a space sufficient to accommodate the device according to this invention, and implanting the device within the cavity.

The invention further includes a method of making a device comprising (a) manufacturing a top endplate for engagement with a top dome portion of a nucleus, such that the top endplate is engaged in a ball and socket configuration with the top dome portion of a nucleus to form a first joint of defined ranges of motion; (b) manufacturing a nucleus comprising a top dome portion, a core portion, and a bottom foot portion; (c) manufacturing a bottom endplate translationally engaged with the bottom foot portion of the nucleus to form a second joint of defined ranges of motion; and (d) assembling the top endplate with the nucleus and assembling the bottom endplate with the nucleus such that, following assembly, super-physiological force is required to disassemble the device. In such a method, the top endplate preferably comprises a nucleus retaining mechanism providing defined degrees of rotational motion of the top endplate about the top surface of the nucleus when the top endplate and the nucleus are engaged with each other in a ball and socket configuration. In such a method, preferably, the bottom endplate comprises a nucleus retaining mechanism which provides defined degrees of planar translational motion of a bottom foot end of the nucleus when the bottom end of the nucleus is translationally engaged within the bottom endplate. This embodiment of the invention preferably further includes (e) manufacturing a sheath, (f) surrounding the nucleus with the sheath; and (g) retaining the sheath in position surrounding said nucleus by an upper and a lower sheath retention ring. The method may further include (h) binding a top aspect of the sheath to the top endplate with an upper retention ring; and (i) binding a bottom aspect of the sheath to the bottom endplate with a lower retention ring. This method may include assembling the device via a snap-fit or a non-snap-fit mechanism by (a) snap-fitting a top portion of the nucleus through an orifice defined in a ring joint stop unitary with the top endplate for rotational retention within a raceway, or (b) assembling a ring joint stop about a middle portion of the nucleus of lower diameter than the top portion of the nucleus, such that following assembly about the nucleus, assembling the ring joint stop with the top endplate to define a raceway within which the nucleus top portion is rotationally retained. The method preferably further comprises snap-fitting the nucleus lower portion through an orifice defined in a nucleus lower portion retention plate unitary with the bottom endplate for retention within a cavity defined within the bottom endplate, or assembling a nucleus lower portion retention plate about a portion of the nucleus narrower than an orifice defined in the nucleus lower portion retention plate and assembling the nucleus lower portion retention plate with the bottom endplate, wherein the orifice is too narrow for the nucleus lower portion to pass through such that the nucleus lower portion is retained within a cavity defined within the bottom endplate.

A further aspect of this invention is a cervical spine total disc replacement device comprising a ring joint stop with a raceway defined therein for constraining motion of a nucleus portion retained within the ring joint stop raceway.

It will further be appreciated that the invention includes a cervical spine nucleus comprising a top dome portion, a core section unitary with or assembled to become unitary with the top dome portion, and a bottom foot section unitary with or assembled to become unitary with a bottom core section, wherein the nucleus is included in a cervical spine total disc replacement device comprising a raceway for retaining the top dome portion within a ring joint stop portion of a top endplate.

It will further be appreciated that the ring joint stop component of the device according to this invention provides a significant advancement in the art as it creates a closed-profile ball-and-socket joint based on a spherical section considerably smaller than a hemisphere. The ring joint stop component simultaneously establishes rotational limits to two independent rotational degrees of freedom. It also provides a soft joint stop that becomes stiffer as the contact force between it and the nucleus increases. The complex mix of cylindrical and spherical surfaces and their position and angles with respect to each other within the ring joint stop that enable the ring joint stop to operate provides an elegant and deceptively simple solution to a long-felt need in the art. The stiffness and strength of the ring joint stop, due to its ring structure, provides a novel motion element in the art. The total device incorporates three mechanical rotational degrees of freedom, in addition to all the flexure degrees of freedom accommodated by the unique nucleus structure and its mode of engagement with the top and bottom endplates. Strain on the nucleus is minimized since the invention can accommodate all large mechanical rotations with the ball-socket joint and smaller, but significant, translational motions by sliding of the foot planar joint before encountering joint limits that result in contact between limiting elements of the endplates and the nucleus. At that point, flexure motion with resistance, provided by selection of nucleus chemical and production processes to exhibit elasticity characteristics chosen to constrain such motion within pre-determined maxima, commences.

Example 5

Sterilization, Kits, Systems, and Preferred Compositions for Inclusion in the Device According to This Invention A wide range of materials and knowledge is available to those skilled in the art for constitution of the nucleus, the sheath or other components of the device according to this invention. In a preferred embodiment according to this invention, the nucleus comprises a DSM Biomedical material selected from the group consisting of: Bionate® Thermoplastic Polycarbonate-urethane (PCU) medical grade polymer for long-term use in the body (has been used in chronic implants for almost two decades); Bionate® II PCU, DSM's Self-Assembling Monolayer End Group (SAME®) technology, enabling customized surface characteristics to address device-specific requirements, making it well-suited for chronically implanted devices; BioSpan® Segmented Polyurethane (SPU), a medical-grade polymer with superior mechanical characteristics that, among other benefits, is designed to withstand high flex fatigue; CarboSil® Thermoplastic Silicone-Polycarbonate-urethane (TSPCU), a copolymer that combines the benefits of silicone and polyurethane to create a material with exceptional toughness and biocompatibility that is also easy to process; Elasthane™ Thermoplastic Polyether-urethane (TPU), a high strength, aromatic, biomedical polymer with a combination of mechanical properties and biological compatibility to support long-term implantation; and. PurSil® Thermoplastic Silicone-Polyether-urethane (TSPU), a strong yet flexible copolymer with proven biocompatibility and biostability. In a further embodiment according to this invention, the top endplate, the bottom endplate, or both comprise human allograft, including wherein only portions thereof comprise bone for bony ingrowth integrated metallic portions thereof included to provide rigidity pending such ingrowth.

What is claimed is:

1. A device comprising:
  a. a top endplate comprising a top surface for engaging with the underside of a superior vertebral body and a bottom surface engaged in a ball and socket configuration with a top dome portion of a resilient nucleus to form a first joint of defined, and mechanically constrained, ranges of motion inherently enforced by the joint structure;
  b. the nucleus comprising a top convexly curvate dome portion, a core portion connecting said curvate top dome portion to a substantially planar bottom foot portion, wherein said nucleus including its dome, core and foot, are either unitary or are connected to each other to form a unitary nucleus and wherein said dome of said nucleus is retained in contact with a mating curvate top endplate undersurface, such that said first joint is a closed-profile joint; and
  c. a bottom endplate translationally engaged with said bottom foot portion of said nucleus to form a second joint of defined, and mechanically constrained, ranges of motion, wherein said foot of said nucleus is retained within a cavity in said bottom endplate in connection with which it is translationally engaged, such that said second joint is a closed profile joint, wherein said first joint and said second joint, in concert, when implanted into an intervertebral space, comprise a closed profile of two joints which are constrained by the resulting mechanical structure to facilitate substantially physiologically acceptable rotational, lateral and flexural motions, when compared with a biological disc in the spine of a recipient which said device is implanted to replace;

wherein said first joint and said second joint each comprises a nucleus retention mechanism providing defined, and mechanically constrained, degrees of motion of said top endplate about the top dome portion of said nucleus and said bottom endplate in relation to the bottom foot portion of said nucleus such that each said mechanism sustains, restrains, constrains, stabilizes, or guides the larger motions required to preserve normal mechanical motion of a spinal joint, while at the same time, said nucleus provides a flexion component to guide and restrain or constrain the finer motions reached at the extremes set by mechanical motion preservation components:

i. wherein the device is assembled by either a snap-fit or a non-snap-fit method for associating device components to each other;
ii. wherein the device further comprises a sheath surrounding said nucleus;
iii. said first joint comprises said top endplate which comprises a Ring-Joint-Stop (RJS) unitary with or assembled to become unitary with said top endplate, wherein said Ring-Joint-Stop either:
   a. comprises an orifice and a raceway, such that said top dome portion of said nucleus snap-fits through said orifice for rotational retention within said raceway; or
   b. an orifice and raceway are defined about the core portion of said nucleus and, once assembled thereabout, retains said dome portion from traversing through said orifice for rotational retention within said raceway;
iv. wherein said bottom endplate comprises a nucleus bottom foot portion retention plate unitary with or assembled to become unitary with said bottom endplate, wherein said retention plate either:
   a. comprises an orifice through which said nucleus bottom foot portion is snap-fit for retention within a cavity defined within said bottom endplate; or
   b. is assembled about a core portion of said nucleus to comprise an orifice with sufficiently small diameter that the bottom foot portion of said nucleus cannot traverse through said orifice;
v. at least one cushion ring which interacts with the Ring-Joint-Stop to protect the RJS and retainer plate from impingement damage that would be caused by rotations exceeding their Range-of-Motion (ROM), by resisting further motion once the RJS contacts a cushion ring; and
vi. said nucleus top dome portion comprises a substantially convex top surface shaped to lubriciously mate with the underside of said top endplate and a bottom surface shaped to lubriciously and translationally mate with said bottom endplate such that said top and bottom endplates, once mated with said resilient nucleus, requires super-physiologic force to disengage from each other.

2. The device according to claim 1 wherein:
   i. said sheath surrounding said nucleus is retained in position by upper and lower sheath retention rings wherein each said upper and lower sheath retention ring binds a top aspect of said sheath to said top endplate and a bottom aspect of said sheath to said bottom endplate, respectively, to thereby securely and imperviously define a chamber about said nucleus by retaining said sheath within sheath retention ring raceways defined circumferentially about said top endplate and said bottom endplate, respectively; and
   ii. said sheath comprises of a thin, extremely elastic, biocompatible material, wherein sterile fluid is optionally included within the chamber delineated between said sheath, said top endplate, and said bottom endplate, wherein said fluid is incorporated during manufacture via a port provided in said bottom endplate or in said top endplate, wherein said port is sealed by a removable port plug.

3. The device according to claim 1 wherein said cavity defined within said bottom endplate permits said nucleus bottom foot portion to translate along a horizontal plane defined by a substantially planar lower internal surface of said bottom endplate.

4. The device according to claim 1 wherein:
   a. said top endplate Ring-Joint-Stop is assembled about a middle portion of said nucleus of lower diameter than said top portion of said nucleus, such that following said assembly about said nucleus, said Ring-Joint-Stop is assembled with said top endplate to define a raceway within which said nucleus top portion is rotationally retained;
   b. said bottom endplate comprising the nucleus bottom foot portion retention plate which is assembled about a portion of said nucleus core portion which is narrower than the orifice defined through said retention plate, when assembled and affixed to said bottom endplate, but which is too narrow for said nucleus bottom foot portion to pass through such that said nucleus bottom foot portion is retained within the cavity defined within said bottom endplate;
   c. axial rotation of said second joint realized by the allowed relative motion between the foot surface and bottom endplate surface of the nucleus is unrestricted regardless of the position of the nucleus foot within said cavity in said bottom endplate, and wherein boundaries dictated by an opening in the bottom endplate nucleus retainer and cavity form an enclosing cavity within which the nucleus foot and, hence, the entire integrated nucleus translates and axially rotates;
   d. spherical mating of the nucleus dome and a mating concavity provided on the underside of the top endplate does not allow translational motion, and wherein flexibility of the nucleus permits y-axis compression-extension, such that, during compression of the nucleus, all three elements of the nucleus, dome, core, and foot have space into which they expand, such that relative rigidity of the top endplate forces the expanded dome to retain the shape of a spherical section;
   e. x-z axis translations of the top endplate and the spherically mated nucleus dome occurs in concert; and
   f. combinations thereof.

5. The device according to claim 4 wherein the device allows six independent motion degrees-of-freedom between said top endplate and said bottom endplate without separation of either said first spherical joint (ball-and-socket) or said second planar joint within the device either prior to or following device implantation, such that said device maintains functional and positional integrity throughout normal operation, including in zero gravity, wherein mechanics of the device allow large mechanical motions of rotation, compression, and translation, while flexibility of the nucleus allows small flexure motions for all degrees of freedom when the joint is at one or more joint stops and wherein said Ring-Joint-Stop is created by mating together an anterior and a posterior Ring-Joint-Stop component to thereby create an enclosing aperture, or orifice which is too narrow to allow the nucleus dome to pass through, resulting in assembly by press-fit, laser weld, or both, into a raceway of said top endplate, including at least one element to limit axial rotation within said raceway.

6. The device according to claim 1 wherein said top endplate comprises or is assembled to comprise a curvate Ring-Joint-Stop comprising:
  i. raised left and right lateral convex cylindrical bearing surfaces which define two angle parameters ($\beta_1$ and $\beta_2$ respectively), within a Ring-Joint-Stop raceway, generated by rotating curvate surfaces of same or different sizes about an x-axis that passes through the center of curvature of said first joint (ball-and-socket), which dictates the ROM of Right-Left Lateral-Bending angle $\mu$ such that $-\beta_2 \leq \mu \leq \beta_1$; ii. raised posterior and anterior convex cylindrical bearing surfaces which define two angle parameters ($\alpha_1$ and $\alpha_2$) within a Ring-Joint-Stop raceway, generated by rotating curvate surfaces of same or different sizes about a z-axis that passes through the center of curvature of said first joint (ball-and-socket), which dictates the ROM of Flexion-Extension angle $\lambda$ such that $-\alpha_2 \leq \lambda \leq \alpha_1$; and
  iii. four cylindrical bearing surfaces in which at least one surface contacts a curvate nucleus dome lip in a curvate line for any rotation angle outside the ROM of either Flexion-Extension or Lateral-Bending, such that, as the rotation angle increases, contact forces increase; and either
  iva. a Ring-Joint-Stop rim, smoothly integrated with and transitioning between each of said four cylindrical bearing surfaces and four, substantially flat, inner-raceway surfaces, wherein said four substantially flat, inner-raceway surfaces provide strength and stiffness to said Ring-Joint-Stop; or
  ivb. a Ring-Joint-Stop rim, which, with respect to the nucleus x-y-z frame of reference and with all four angle parameters equal the same value $\alpha$, that facilitates and limits the ROM of both Flexion-Extension angle ($\lambda$) and Lateral Bending angle ($\mu$) within the range $-\alpha \leq \lambda, \mu \leq \alpha$, as follows:
    a) it allows any sequence of rotations, that at no time results in an equivalent rotation that would require, as part of its implementation, a rotation about some axis in the x-z plane whose magnitude is greater than $\alpha$ degrees;
    b) it permits any sequence of rotations satisfying a), which includes Axial (y-axis) rotations, then such Axial rotations move without constraint, whereas any Axial rotation in a sequence of rotations that does not satisfy condition a), is constrained by the RJS;
    c) it constrains a sequence of rotation motions that does not satisfy condition a) by contacting the cushion ring included in said device so as to protect the RJS and a retainer plate from impingement damage that would be caused by rotations exceeding either Flexion-Extension or Lateral-Bending Ranges-of-Motion (ROMs), and, by resisting further motion once the RJS contacts the cushion ring, such that said engagement of the RJS and cushion ring provides a soft stop with increasing resistance as the angle increases beyond $\alpha$ degrees, eventually producing a hard stop; and
    d) it comprises a curvate or conic shaped underside portion which participates in resisting either out-of-range, or near out-of-range rotations through curvate line or linear contact, respectively, with a cushion ring thickness designed for such contact.

7. The device according to claim 6 comprising element (ivb) wherein said cushion ring is adhered to said top plate.

8. The device according to claim 1 wherein said cushion ring is adhered to said top plate.

9. A method comprising:
  a. removing a damaged intervertebral disc to create a space sufficient to accommodate the device according to claim 1; and
  b. implanting said device within said cavity.

* * * * *